United States Patent
Hunziker et al.

(10) Patent No.: US 10,513,585 B2
(45) Date of Patent: Dec. 24, 2019

(54) AMPHIPHILIC POLYMER SYSTEMS

(71) Applicant: UNIVERSITÄTSSPITAL BASEL, Basel (CH)

(72) Inventors: Patrick Hunziker, Binningen (CH); Kegang Liu, Basel (CH)

(73) Assignee: UNIVERSITÄTSSPITAL BASEL, Basel (CH)

( * ) Notice: Subject to any disclaimer, the term of this patent is extended or adjusted under 35 U.S.C. 154(b) by 159 days.

(21) Appl. No.: 15/539,490

(22) PCT Filed: Dec. 23, 2015

(86) PCT No.: PCT/EP2015/081154
§ 371 (c)(1),
(2) Date: Jun. 23, 2017

(87) PCT Pub. No.: WO2016/102663
PCT Pub. Date: Jun. 30, 2016

(65) Prior Publication Data
US 2017/0369655 A1  Dec. 28, 2017

(30) Foreign Application Priority Data
Dec. 23, 2014  (EP) .................................. 14199975

(51) Int. Cl.
| | | |
|---|---|---|
| *C08G 77/452* | (2006.01) | |
| *A61K 49/00* | (2006.01) | |
| *A61K 9/00* | (2006.01) | |
| *A61K 47/34* | (2017.01) | |
| *A61K 9/107* | (2006.01) | |
| *A61K 47/55* | (2017.01) | |
| *A61K 47/59* | (2017.01) | |
| *A61K 47/69* | (2017.01) | |
| *A61K 31/337* | (2006.01) | |
| *A61K 31/519* | (2006.01) | |
| *A61K 31/704* | (2006.01) | |
| *A61K 31/713* | (2006.01) | |

(52) U.S. Cl.
CPC .......... *C08G 77/452* (2013.01); *A61K 9/0053* (2013.01); *A61K 9/107* (2013.01); *A61K 31/337* (2013.01); *A61K 31/519* (2013.01); *A61K 31/704* (2013.01); *A61K 31/713* (2013.01); *A61K 47/34* (2013.01); *A61K 47/551* (2017.08); *A61K 47/59* (2017.08); *A61K 47/6907* (2017.08); *A61K 49/0032* (2013.01); *A61K 49/0041* (2013.01); *A61K 49/0054* (2013.01); *A61K 49/0082* (2013.01)

(58) Field of Classification Search
CPC .. C08G 77/452; A61K 31/713; A61K 31/704; A61K 31/337; A61K 31/519; A61K 47/6907; A61K 47/59; A61K 47/551; A61K 47/34; A61K 49/0082; A61K 49/0054; A61K 49/0041; A61K 49/0032; A61K 9/107; A61K 9/0053
See application file for complete search history.

(56) References Cited

U.S. PATENT DOCUMENTS

2008/0305149 A1  12/2008  Hirt et al.

FOREIGN PATENT DOCUMENTS

| | | |
|---|---|---|
| WO | WO 00/37541 A1 | 6/2000 |
| WO | WO 01/32146 A2 | 5/2001 |
| WO | WO 2008/152490 A2 | 12/2008 |
| WO | WO 2008/153966 A1 | 12/2008 |
| WO | WO 2011/127256 A1 | 10/2011 |
| WO | WO 2016/102663 | 6/2016 |

OTHER PUBLICATIONS

Broz et al., "Cell targeting by a generic receptor-targeted polymer nanocontainer platform," Journal of Controlled Release, 2005, 102:475-488.
International Search Report for International Patent Application No. PCT/EP2015/081154, prepared by the International Search Authority, dated Feb. 22, 2016, 4 pages.
Lee et al., "Synthesis and Micellar Characterization of Amphiphilic Diblock Copolymers Based on Poly (2-ethyl-2-oxazoline) and Aliphatic Polyesters," Macromolecules, 1999, 32:1847-1852.

*Primary Examiner* — Robert S Jones
(74) *Attorney, Agent, or Firm* — Hoxie & Associates LLC

(57) ABSTRACT

The preparation of poly-2-oxazoline amphiphilic polymers and copolymers is described. Self-assembled particles comprising these amphiphilic polymers and which are useful for the targeted delivery of therapeutic and diagnostic agents are also described.

27 Claims, 1 Drawing Sheet

1A

1B

AMPHIPHILIC POLYMER SYSTEMS

CROSS REREFERENCE TO RELATED APPLICATIONS

Figure 1:
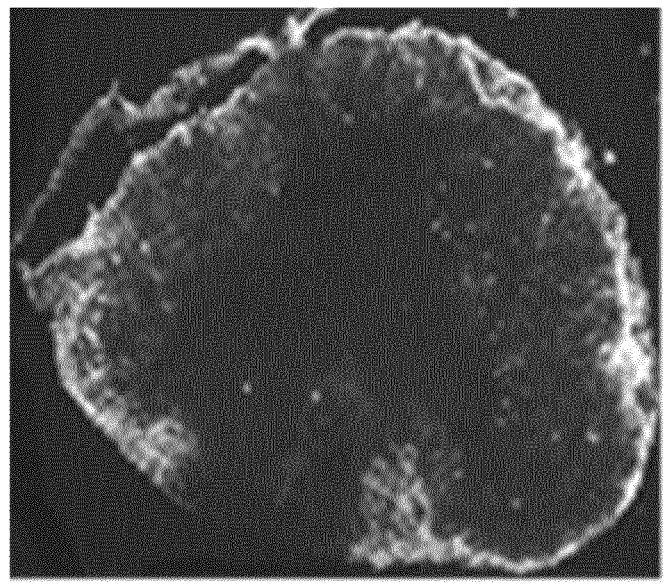
Figure 1:
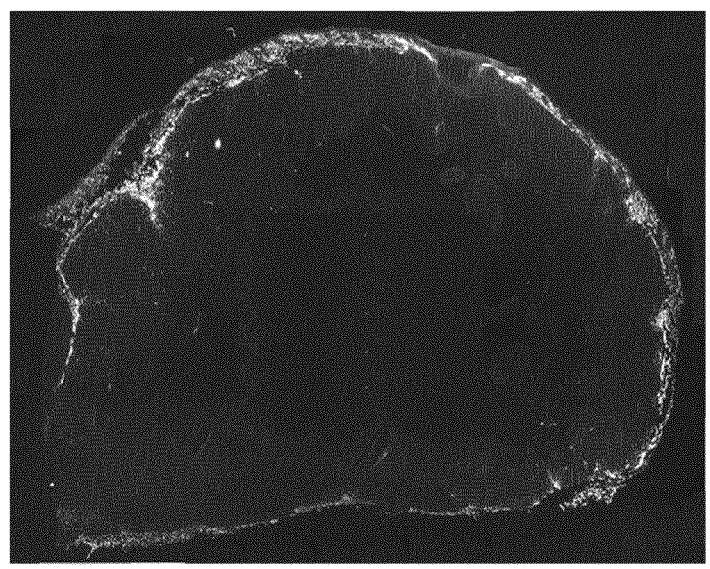

This application is a United States National Stage Application under 35 USC § 371 of International Application No. PCT/EP2015/081154 filed Dec. 23, 2015, which claims priority to EP 14199975.5 filed Dec. 23, 2014, the contents of each of which are incorporated herein by reference.

FIELD

The present invention relates to self-assembled particles comprising amphiphilic polymers, their methods of preparation and their therapeutic and/or diagnostic use. The invention also relates to the amphiphilic polymers and their methods of preparation.

BACKGROUND

Drug delivery and diagnostic systems based on target-specific polymeric vehicles have become of interest in recent years.

Targeted drug delivery, i.e. delivery of a therapeutic drug to a specific tissue or diseased cell is associated with a number of advantages. With a targeted approach, systemic toxicity can be reduced or avoided; drug dosing may also be reduced. The problem of poor solubility, of an otherwise efficacious drug candidate may be also overcome. The use of polymeric delivery systems is also advantageous in that these may be retained and circulated for a longer period of time, thus bypassing the typically faster clearance of the active agent from the body. In respect of targeted delivery of diagnostic agents, an improved localization of an imaging agent to a specific organ or tissue type can bring about a more assured diagnosis.

An example of a polymeric drug delivery system is those that are based on PEG (polyethylene glycol). PEG-polymer-conjugated small molecular pharmaceuticals or bio-pharmaceuticals have been developed and indeed, many of these conjugates have been found to have improved properties such as increased drug solubility, half-life extension, low cytotoxicity and immunogenicity. Although PEG, to certain degree remains a gold-standard in polymer-based biomedical applications, there are however disadvantages and limitations in respect of this type of polymer. For example, hypersensitivity and the formation of PEG antibodies have been observed in several instances. In particular, PEG, has somewhat limited functionality available for modification and for orthogonal functionalization.

Other polymer systems have also been investigated such as those based on poly-2-oxazoline (also abbreviated as PDX). This type of polymer are useful in biomedical applications as these also have generally been found to be biocompatible, and moreover, tend to have immunological 'stealth' i.e. non-specific binding properties so that recognition by the immune defence system and fast clearance is avoided.

Amphiphilic polymer systems comprising poly-2-oxazoline as a structural element have been developed.

For example, US2008/0305149 describes the preparation amphiphilic triblock segmented copolymers comprising poly-2-methyloxazoline and polydimethylsiloxane segments (i.e. poly(2-methyloxazoline)-block-poly(dimethylsiloxane)-block-poly(2-methyloxazoline) triblock polymers, or abbreviated as PMOXA-PDMS-PMOXA), and their use in making vesicles with a mucoadhesive outer surface. It is described that these vesicles may be used for delivery of an active agent, which are encapsulated within the vesicle. Such vesicles however cannot be readily be modified for targeted drug delivery. The amphiphilic polymers used to prepare the vesicles are limited in terms of options for further functionalization.

Broz et al (J. Control. Release 2005 (102) 475-488) describe nanocontainers based also on PMOXA-PDMS-PMOXA amphiphilic polymers. In this instance, the amphiphilic polymers are terminally functionalized with biotin. The biotin ligand is used as a means for linking the nanocontainer, with streptavidin as a linchpin, to a receptor specific ligand, i.e. a polyguanylic acid (polyG) oligonucleotide that is also biotinylated. Although the biotin-streptavidin bond is strong, it is however not irreversible; this kind of linkage is also not the most suitable for in vivo use.

It is therefore an object of the present invention to introduce novel poly-2-oxazoline amphiphilic polymers and copolymers, for use in the preparation of self-assembled particles, and which overcomes any of the limitations and disadvantages of the current polymer systems. A further object is to develop self-assembled particles which may be used for targeted delivery of a therapeutic agent or diagnostic agent.

SUMMARY OF THE INVENTION

In a first aspect, the invention relates to a self-assembled particle comprising an amphiphilic polymer of the general Formula (I):

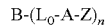

wherein n is 1 or 2;
B is a hydrophobic polysiloxane segment;
$L_0$ is a divalent linker segment;
A is a hydrophilic poly-2-oxazoline copolymer segment; and
wherein Z is a terminal group or a linker conjugated to a ligand.

In particular, the present invention provides self-assembled particles such as micelles comprising an amphiphilic polymer of the general Formula (I), which are useful for targeted delivery of therapeutic agents, or diagnostic agents. In one aspect, the self-assembled particles may comprise an amphiphilic polymer of general Formula (I) comprising a receptor-specific ligand that is useful for targeting specific cells and tissues. In another aspect, the self-assembled particles comprise an amphiphilic polymer of the general Formula (I) which is conjugated to a therapeutic agent or a diagnostic agent. In yet another aspect, self-assembled particles are suitable for use in gene delivery and gene therapy and comprise an amphiphilic polymer of the general Formula (I) comprising amine-based functionality.

The invention further relates to self-assembled particles comprising an amphiphilic polymer of Formula (I) in combination with an amphiphilic polymer of Formula (II):

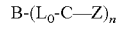

wherein n is 1 or 2;
B is a hydrophobic polysiloxane segment;
$L_0$ is a divalent linker segment;
C is a hydrophilic poly-2-oxazoline homopolymer segment;
and wherein Z is a terminal group or a linker conjugated to an ligand. In one aspect, the self-assembled particles of the invention may also comprise at least one amphiphilic polymer of Formula (II) wherein Z is a terminal group and at least one amphiphilic polymer of Formula (II) wherein Z is a ligand conjugated to a linker.

In a further aspect, the invention relates to self-assembled particles in the form micelles or vesicles.

In yet a further aspect, the invention relates to the amphiphilic polymers of general Formula (I) and methods for their preparation.

DETAILED DESCRIPTION OF THE INVENTION

In a first aspect, the invention relates to a self-assembled particle comprising an amphiphilic polymer of the general Formula (I):

$$B\text{-}(L_0\text{-}A\text{-}Z)_n$$

wherein n is 1 or 2;
B is a hydrophobic polysiloxane segment;
$L_0$ is a divalent linker segment;
A is a hydrophilic poly-2-oxazoline copolymer segment; and
Z is a terminal group or a linker conjugated to a ligand.

A self-assembled particle, as understood herein, refers to a structure comprising one or more amphiphilic polymers, and which is formed as a result of an equilibrium of attractive and repulsive forces between the polymers and an aqueous bulk solution. Self-assembly refers to the aggregation of such polymers in order to minimize and optimize hydrophobic-water interface effects. As a result of the aggregation and due to molecular interactions (for example, steric repulsion) between the amphiphilic components as such, particles of a definable structure may be formed. Typically, a minimum concentration of amphiphiles is required for the transition of free solute to aggregate (often termed minimum aggregate concentration) into particles. As understood herein, the term particle refers to any kind of definable structure that is formed from the aggregation of amphiphiles, including but not limited to micelles and vesicles, and any of their morphological variations. Particularly preferred are self-assembled particles in the form of micelles.

The term amphiphilic polymer as used herein refers to a polymer comprising structural elements having an affinity towards water or an aqueous environment, as well as structural elements having an affinity towards non-polar, hydrophobic or lipidic environments. Typically, an amphiphilic polymer or compound comprises at least one hydrophilic portion and at least one hydrophobic (or lipophilic) portion. The hydrophobic segment is more readily dissolved in, or wetted by, non-polar solvents, such as hydrocarbons, than by water. The property of the hydrophilic segment on the other hand has a higher affinity for a more polar environment and is generally more readily wetted or dissolved by water.

Further, a polymer is a compound which is formed from the chemical union of two or more repeating units or monomers. As used herein, a copolymer refers to a polymer derived from two or more different monomers, while a homopolymer refers to a polymer consisting of a single repeating monomer unit. The term block copolymer or block polymer refers to a polymers comprising of at least two different polymer segments, wherein each polymer segment typically comprise two or more adjacent units or monomers of the same kind.

In one embodiment, the amphiphilic polymer of the general Formula (I) comprises one hydrophobic polysiloxane segment B and one hydrophilic copolymer segment A; in other words, n is an integer of 1. More preferably, n is an integer of 2 so that the amphiphilic polymer of Formula (I) comprises a hydrophobic polysiloxane segment B and two hydrophilic copolymer A segments, i.e. (Z-A-$L_0$)-B-($L_0$-A-Z)

More specifically, the hydrophobic polysiloxane segment B may be a polysiloxane of Formula (III)

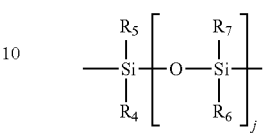

wherein j is an integer from 5-1000; and wherein 80-100% of $R_4$, $R_5$, $R_6$, $R_7$ are, independently of one another, C1-C10 alkyl, and 0-20% of $R_4$, $R_5$, $R_6$, $R_7$ are independently of one another, C3-C12 alkenyl, unsubstituted C1-C4 alkyl- or C1-C4 alkoxy-substituted phenyl, fluoro(C1-C18 alkyl), or cyano(C1-C12 alkyl).

Preferably, j is an integer from 10 to 300. In a particular embodiment, j is an integer from 10 to 150.

Preferably, 90-100% of the $R_4$, $R_5$, $R_6$, $R_7$ are independently selected from alkyl bearing up to 6 carbons, in particularly up to 4 carbons.

In another embodiment, 0-10% of $R_4$, $R_5$, $R_6$, $R_7$ are selected independently from C3-C8 alkenyl, unsubstituted or methyl-, ethyl-, methoxyl-, or ethoxyl-substituted phenyl, fluoro(C1-C8 alkyl) or cyano(C1-C4 alkyl).

In a particularly preferred embodiment, $R_4$, $R_5$, $R_6$, $R_7$ are all methyl or all ethyl, i.e. the hydrophobic polysiloxane segment B is selected from polydimethylsiloxane or polydiethylsiloxane, wherein the segment preferably comprises 10 to 150 monomer units.

The divalent linker segment $L_0$ provides a means for covalently linking the hydrophobic polysiloxane segment B to the hydrophilic poly-2-oxazoline copolymer segment A.

The term linker, interchangeable with the term linkage, linking element or spacer, when used herein in respect of a polymer, ligand or any other chemical entity refers to covalent bonding between at least two distinct chemical moieties. The linker may be an intermediate moiety, acting as a spacer between said two moieties, the intermediate moiety or spacer being formed also from one or more chemical reactions which give rise to covalent bonding. In such cases, the linker may be described as being divalent. In other cases, a linker may be multivalent i.e. function as a linking means for more than two moieties.

In particular, $L_0$ is represented by the formula $R_8(Q)_u$, wherein $R_8$ is an alkylene or arylene group containing up to 20 carbon atoms, and Q is selected from —O—, —S—, —S—S—, —$NR_9$—, —NHC(O)—, —C(O)NH—, —OC(O)NH—, —NHC(O)O—, —OC(O)—, C(O)O—, —NHC(O)NH—, —SC(O)—, —C(O)S—, —NHC(S)NH—,

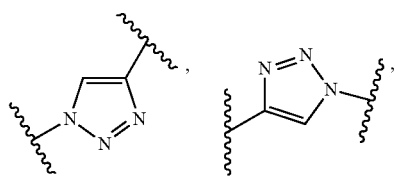

wherein $R_9$ is hydrogen or C1-C4 alkyl and u is 0, 1, or 2.

The hydrophilic poly-2-oxazoline copolymer segment A comprises at least two 2-substituted 2-oxazoline monomers, i.e. the copolymer is obtainable from the copolymerization of at least two 2-substituted oxazoline monomers. The 2-oxazoline monomers may be selected from 2-oxazoline monomers substituted with aliphatic or aromatic moieties, for example 2-alkyl-2-oxazolines such as 2-methyl-2-oxazoline, 2-ethyl-2-oxazoline, 2-propyl-2-oxazoline, or 2-aryl-2-oxazolines such as 2-phenyl-2-oxazoline. Further preferred are 2-oxazoline units which may be used for the preparation of the hydrophilic poly-2-oxazoline copolymer segment A are those substituted and functionalized at the 2-position with moieties comprising functional groups such as an amine, an azide, an alkyne, an aldehyde, an acetal, an alcohol, a carboxylic acid, an activated carboxylic acid, an oxyamine, a ketone, a ketal, an ester, a maleimide, a vinyl sulfone, an orthopyridyl disulfide or a chloroformate, which can be further chemically modified and used as a handle for conjugation with further chemical entities. The hydrophilic poly-2-oxazoline copolymer segment A may be obtainable from the copolymerization of two or more of these types of 2-oxazoline monomers.

In a particular embodiment, segment A comprises two or more 2-substituted 2-oxazoline monomers, wherein at least one of the monomers is selected from a 2-alkyl-2-oxazoline, such as 2-methyl-2-oxazoline, or a 2-aryl-2-oxazoline. In such cases, segment A is obtainable from the copolymerization of at least two 2-substituted 2-oxazoline monomers, wherein at least one of the monomers is a 2-alkyl-2-oxazoline ora 2-aryl-2-oxazoline.

In general, the term alkyl as used herein includes both straight and branched chain hydrocarbon groups comprising from 1 to 40 carbons in the main chain. The hydrocarbon chain may be saturated or unsaturated (i.e. comprise double bonds (alkenyl) and/or triple bonds (alkynyl)). The hydrocarbon chain may also be cyclic, for example cyclopropyl, cyclobutyl, cyclopentyl, cyclohexyl, cycloheptyl, cyclooctyl, or comprise a portion which is cyclic (polycyclic alkyl groups are also included, for example, but not limited to cholesteryl, adamantyl, norbornyl, bicycle[2.2.2]octyl). The hydrocarbon chain of the alkyl group may be interrupted with heteroatoms selected from one or more atoms such as oxygen, nitrogen, sulphur or silicon. Each alkyl group may optionally be substituted through available carbon atoms with substituents which include, for example, alkyl, halo(F, Cl, Br, I), haloalkyl (e.g., $CCl_3$ or $CF_3$), alkoxyl, aryloxyl, alkylthio, hydroxyl, methoxy, carboxyl, epoxy, alkyloxycarbonyl, alkylcarbonyloxy, amino, carbamoyl (e.g., $NH_2C(=O)$— or $NHRC(=O)$—, wherein R is an alkyl or an aryl), urea(—$NHCONH_2$), thiourea(—$NHSONH_2$), alkylurea, aryl, ether, ester, thioester, nitrile, nitro, amide, carbonyl, oxo, carboxylate, thiol, alkyl sulfide, aryl sulphide, sulfone, sulfoxide, trialkylsilyl, dialkylarysilyl, alkyldiarylsilyl and triarysilyl. Examples of simple alkyls include, without limitation, propyl, butyl, pentyl, hexyl, heptyl, octyl, and nonyl.

As used herein, the term aryl refers to monocyclic and bicyclic aromatic hydrocarbon groups containing 6 to 12 carbons in the ring portion or aromatic groups including 5- and 6-membered single aromatic ring. Aryl groups may be optionally substituted through available carbon atoms with substituents as defined above. The aromatic ring system may include from 1 to 4 heteroatoms such as sulphur, oxygen or nitrogen. Examples of above aryls include, without limitation, phenyl, tolyl, hydroxyphenyl, benzyl, naphthyl, biphenyl, pyrrole, furan, thiophene, thiazole, isothiaozole, imidazole, triazole, tetrazole, pyrazole, oxazole, isoxazole, triazine, triazine, tetrazine, pyridine, pyrazine, pyridazine, and pyrimidine.

In a further preferred embodiment, segment A is obtainable from the copolymerization of 2-methyl-2-oxazoline and an azide-functionalized 2-oxazoline monomer, especially a 2-4-azidoalkyl-2-oxazoline such as 2-(4-azidobutyl)-2-oxazoline.

In another aspect, the poly-2-oxazoline copolymer segment A may be selected from a random poly-2-oxazoline copolymer, a diblock poly-2-oxazoline copolymer and a triblock poly-2-oxazoline copolymer. A random poly-2-oxazoline copolymer comprises of at least two different 2-oxazoline monomer units which are randomly distributed in the copolymer, whereas a block poly-2-oxazoline copolymer comprises at least two different polymer segments, each independently comprising a specific 2-oxazoline monomer. A block copolymer comprising two segments is particular preferred (i.e. a diblock poly-2-oxazoline copolymer), as are block copolymers comprising three segments (i.e. a triblock copolymer). The random poly-2-oxazoline copolymers are obtainable by the simultaneous addition of the at least two poly-2-oxazoline monomer units during the copolymerization process. In contrast, the block copolymers are obtainable by sequential addition of the poly-2-oxazoline monomers during the copolymerization process.

The backbone of segment A is the poly-2-oxazoline copolymer. However, in some embodiments, the poly-2-oxazoline copolymer is further conjugated to a chemical moiety having, for example, a therapeutic or diagnostic function. In particular, the self-assembled particle may comprise an amphiphilic polymer of Formula (I) wherein the hydrophilic poly-2-oxazoline copolymer segment A is conjugated with a diagnostic agent, a therapeutic agent, or a ligand such as an antibody, an antigen-binding fragment (fab) fragment, a single domain antibody, an oligonucleotide, a polypeptide or a carbohydrate. Preferred ligands are biotin, folate or a peptide.

Preferred therapeutic agents are pharmaceutically active ingredients or drugs such as lipid-modifying agents, immunosuppressants, corticosteroids, anti-inflammatory agents, antithrombotics, analgesics, antibacterial agents, or agents for photodynamic therapy. Particularly preferred are chemotherapeutic and antineoplastic agents, for example doxorubicin or taxol.

Preferred diagnostic agents include fluorescent dyes such as near-infrared (NIR) fluorescent dyes, radiolabels, PET-imaging agents, MRI-imaging agents, sensitizers, and a photoacoustic imaging agent. Examples of diagnostic agents include fluorescein, rhodamine, cyanines, phthalocyanines, BODIPY and their derivatives. Such diagnostic agents may also provide therapeutic activity; for example, function as an agent for photodynamic therapy.

In this context, the term conjugated refers to the linking of the agents or ligands to the poly-2-oxazoline copolymer segment via covalent bonding. The conjugation preferably comprises a covalent bond that can be cleaved or hydrolysed under physiological conditions. While physiological conditions may vary depending on the local micro-environment of a given tissue, organ or cellular environment in respect of for example pH, redox environment, etc., it is generally understood that physiological condition refers to temperatures of about physiological temperature, about 20° C. to about 40° C.; in particular 33-37° C. and a pH of about 6-8. The hydrolysis or cleavage of the covalent bond may also be enzymatic. For the purpose of drug delivery, a cleavable or hydrolysable bond is particularly preferred for conjugation of the therapeutic agents to the copolymer segment. Alternatively, the conjugation may be in the form of a non-hydrolysable bond or a bond that is not prone to cleavage under physiological conditions or by any native enzymes.

As used herein, the terms 'a diagnostic agent' or 'a therapeutic agent' or 'a ligand' is not limited to the singular, i.e. a single compound conjugated to the polymer. As the polymer comprises repeating units, it is to be understood that more than one unit may be conjugated to a diagnostic or therapeutic agent or a ligand. It is also to be understood that not all of the repeating units of the polymer may be conjugated to a diagnostic agent, therapeutic agent or ligand. For example, at least about 1% or about 10% or at or at least about 60% of the poly-2-oxazoline co-polymer segment repeating units may be conjugated to a diagnostic agent, a therapeutic agent, a ligand or a combination thereof. In one embodiment, the poly-2-oxazoline copolymer segment A may be conjugated to both a diagnostic and a therapeutic agent. In another embodiment, the poly-2-oxazoline copolymer segment A may be conjugated to more than one therapeutic agent.

In a further specific embodiment, the self-assembled particle comprises an amphiphilic polymer of Formula (I) wherein the poly-2-oxazoline copolymer segment A comprises a segment of Formula (Ia):

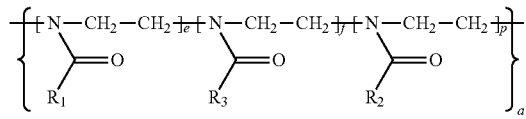

wherein $R_1$ and $R_3$ are independently selected from a linker conjugated to a functional group selected from an amine, an azide, an alkyne, an aldehyde, an acetal, an alcohol, a carboxylic acid, an activated carboxylic acid, an oxyamine, a ketone, a ketal, an ester, a maleimide, a vinyl sulfone, an orthopyridyl disulfide and a chloroformate; and a linker conjugated to a therapeutic, diagnostic or ligand. $R_2$ is independently selected from C1-C20 alkyl and aralkyl groups. Moreover, e, f, are integers independently selected from 0-500, provided that e and f are not simultaneously be selected as 0; p is an integer selected from 2-500; and a is selected from ran and block, wherein ran indicates a random copolymer whose units as defined by e, f and p are in random, whereas block indicates a block copolymer whose units as defined by e, f, and p are sequential segments.

The functional groups may serve as handles for further chemical modification or functionalization. In other cases, they may be functional groups which are already structurally relevant for the final amphiphilic polymer product and require no further modifications. In a particularly preferred embodiment, R1 and R3 are independently selected from a linker, preferably a C1 to C30 alkylene or an arylene, conjugated to an amine or an azide.

In a further preferred embodiment, the self-assembled particle comprises an amphiphilic polymer of Formula (I) wherein Z is a terminal group. Z is directly linked to an end terminus of the poly-2-oxazoline polymer segment A, and may be directly derived (or modified) from the nucleophile that is used to quench or terminate the poly-2-oxazoline copolymerization reaction. Preferably, Z is selected from a terminal group of formula —$X_1$-$Q_0$, wherein $X_1$ is selected from —O—, —S—, —NH—, —$NR_{10}$—,

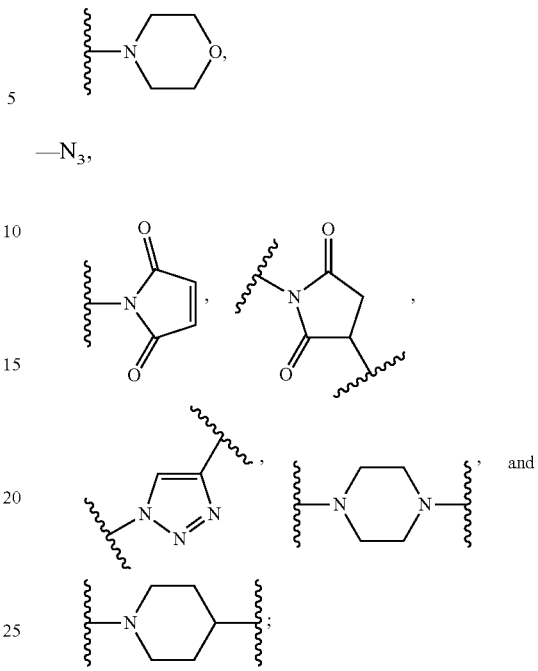

and wherein $Q_0$ is absent or selected from H, unsubstituted or substituted alkyl, alkenyl, aralkyl, alkynyl, heterocyclyl or aryl, —C(O)—$(CH_2)_q$—COOH, —C(O)O—$R_{10}$, —$(CH_2)_q$—C(O)O—$R_{10}$, —C(O)$R_{10}$, —NHC(O)—$(CH_2)_q$—$N_3$, —$(CH_2)_q$—$N_3$, and —S$R_{10}$, wherein $R_{10}$ is selected from unsubstituted or substituted alkyl, alkenyl, aralkyl group and q is an integer from 1 to 10. Most preferably, Z is hydroxyl (—OH).

Alternatively, the self-assembled particle comprises an amphiphilic polymer of Formula (I) wherein Z is a linker conjugated to a ligand that is useful for targeting specific cells and tissues. The ligand is preferably a receptor-specific ligand (for example, a tumour-receptor specific ligand) which enables the self-assembled particle to target, interact and bind to a specific type of receptor, cell, or tissue. The ligand may be selected from a small molecule, an antibody, an antigen-binding fragment (fab), a single domain antibody, an oligonucleotide, a peptide, and a carbohydrate. Particularly preferred ligands are folate and its derivatives, biotin and peptides.

Examples of ligands include, but are not limited to, RGD (arginylglycylaspartic acid) and RGD-containing peptides and their analogues for targeting integrin-expressing cells; EGF and peptides targeting EGF-receptor expressing cells; PD1 and peptides targeting Neuropilin 1; adenoviral fibre protein and peptides for targeting Coxsackie-adenoviral receptor (CAR) expressing cells; ApoE and peptides for LDL receptor targeting; von Willebrand's factor and peptides for targeting exposed collagen; melanotropin (alpha MSH) peptides, transferrin, somatostatin peptides and FGF2 for tumor targeting; vascular endothelial cell growth factor for targeting endothelial cells; folate and its analogues for targeting tumor cells having cell-surface receptors, sialyl lewis for targeting a region of inflammation.

The linker, aside from being a connecting means of the ligand to the end of the poly-2-oxazoline polymer, may also be useful for facilitating the positioning of the ligand in the self-assembled particle, and for ensuring adequate presentation of the ligand for tissue and cell binding. The linker may comprise a hydrolysable covalent bond, or alternatively, no hydrolysable covalent bonds.

In particular, Z may be a linker conjugated to a ligand represented by the formula -$L_3$-$R_{11}$, wherein $L_3$ is selected from —S—, —O—, —OC(O)—, —OC(O)NH—, —NHC(O)—, —NHC(O)NH, —NHC(S)NH—, —NHC(O)O—,

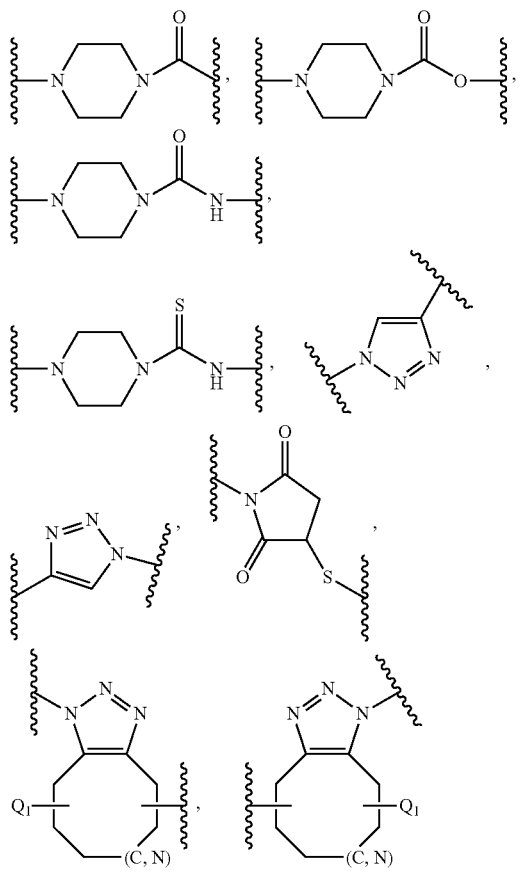

wherein $Q_1$ represents one or more substituents;
and wherein $R_{11}$ is a ligand selected from a small molecule, an antibody, an antigen-binding fragment (fab), a single domain antibody, an oligonucleotide, a polypeptide and a carbohydrate, and in particular from folate, biotin and peptides.

The self-assembled particles that are formed predominantly with an amphiphilic polymer of Formula (I) as a main structural component in a particularly preferred embodiment comprise an amphiphilic polymer of Formula (I) wherein B is a polydimethylsiloxane segment, the poly-2-oxazoline copolymer segment A comprises at least one poly-2-methyloxazoline block, and Z is a terminal group.

In another aspect of the invention, the self-assembled particle comprises an amphiphilic polymer of the Formula (II):

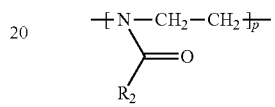

wherein n is 1 or 2;
B is a hydrophobic polysiloxane segment;
$L_0$ is a divalent linker segment;
C is a hydrophilic poly-2-oxazoline homopolymer segment;
and wherein Z is selected from a terminal group or a linker conjugated to an ligand.

The hydrophobic polysiloxane B, the divalent linker segment $L_0$ and the Z terminal group or linker conjugated to a ligand are as defined above for Formula (I).

The hydrophilic poly-2-oxazoline homopolymer segment C comprises a polymer that is obtainable from the polymerization of any 2-substituted 2-oxazoline monomer; particularly preferred are 2-alkyl or 2-aryl substituted 2-oxazoline monomers. In a particularly preferred embodiment, the amphiphilic polymer of Formula (II) comprises a poly-2-methyl-oxazoline segment. Moreover, the poly-2-oxazoline homopolymer segment C may optionally comprise at least 5 and up to 50 or more units of the 2-oxazoline monomer. Preferably, the poly-2-oxazoline homopolymer C segment comprises between 5-30 monomer units.

The amphiphilic polymer of Formula (II) may comprise a segment C of Formula (II-a):

$$-\!\!\left[\!\!\begin{array}{c}N-CH_2-CH_2\\|\\C=O\\|\\R_2\end{array}\!\!\right]_{\!\!p}\!\!-$$

wherein $R_2$ is selected from C1-C20 alkyl or aralkyl group; and p is an integer selected from 2-500.

In a particular embodiment of an amphiphilic polymer of Formula (II) comprising a segment C of Formula (II-a), Z is of the formula -$L_3$-$R_{11}$ as described above, in particular wherein $L_3$ is a triazole linker. In such cases, the triazole linker is a result of the conjugation of the ligand or ligand derivative to the terminal end of the amphiphilic polymer of Formula (II) or (IIa) by means of an azide-alkyne 1,3-dipolar cycloaddition.

In an embodiment, a self-assembled particle comprises a polymer of Formula (IV):

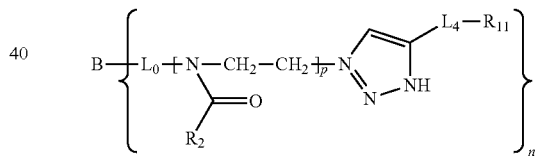

wherein $L_4$ is a linking group comprising a C1-C20 alkylene or arylene group, or a C1-C20 alkylene or arylene group, which may be interrupted by one or more of the heteroatoms O, N or S (e.g. —O—$CH_2CH_2$—O—, —$CH_2$NH—, —$CH_2$—S—S—$CH_2$—$CH_2$—O—); with p preferably being in the range from 5 to 100, in particular 20 to 40; and wherein B, $L_0$, $R_2$ and $R_{11}$ are as described above. Preferably, $R_{11}$ is a ligand selected from a small molecule, antibody, antigen-binding fragment (fab), single domain antibody, oligonucleotide, a carbohydrate, and in particular from folate, biotin or a peptide.

In another particular embodiment of the invention, the self-assembled particle is a micelle comprising at least one amphiphilic polymer of Formula (II) wherein Z is a terminal group.

In yet another embodiment, a self-assembled particle is preferably a micelle and comprises at least one amphiphilic polymer of Formula (II) wherein Z is a terminal group, and at least one amphiphilic polymer of Formula (II) wherein Z is a linker conjugated to a ligand.

The ligand that is featured on the at least one amphiphilic polymer of Formula (II), wherein Z is a linker conjugated to a ligand may be selected from an antibody, an antigen-binding fragment (fab), a single domain antibody, an oligonucleotide, a polypeptide and a carbohydrate. Such ligands are preferably receptor-specific ligands, i.e. such ligands are able to specifically and/or selectively bind directly to a cell or tissue receptor, for example a tumor-receptor-specific ligand. Among the preferred receptor-specific ligands are folate-receptor ligands.

The receptor-specific ligand of these amphiphilic polymers of Formula (II) may also be a small molecule. The small molecule ligand may be natural, or may be a semi-synthetic or fully synthetic organic compound. Among the preferred small molecular ligands are folate receptor ligands such as folate (folic acid) or a derivative thereof, or methotrexate.

In one preferred embodiment, the invention relates to self-assembled particles comprising at least one amphiphilic polymer of Formula (II) wherein Z is a terminal group, wherein the self-assembled particle is a micelle; and wherein the self-assembled particle comprises at least one amphiphilic polymer of Formula (II) wherein Z is a linker conjugated to folate-receptor ligand, preferably folate or a derivative thereof.

In another embodiment, the micelles may further comprise an amphiphilic polymer of Formula (II), wherein Z is a linker conjugated to a therapeutic or a diagnostic agent.

In another embodiment of the invention, the self-assembled particle comprises at least one amphiphilic polymer of Formula (II) wherein Z is a terminal group, and at least one amphiphilic polymer of Formula (II) wherein Z is a linker conjugated to a ligand, wherein the ligand is a receptor-specific ligand, for example folate or a derivative thereof, a peptide, and also other small molecules that are receptor-specific ligands; or a ligand selected from an antibody, an antigen-binding fragment (fab), a single domain antibody, an oligonucleotide, a polypeptide and a carbohydrate.

In any of the above embodiments, it is further preferred that these micelles or self-assembled particle which comprises at least one amphiphilic polymer of Formula (II) wherein Z is terminal group, and at least one amphiphilic polymer of Formula (II) wherein Z is a linker conjugated to a ligand, comprise said polymers wherein the hydrophobic segment B is a polydimethylsiloxane and wherein the hydrophilic segment C is a poly-2-methyl-oxazoline. Preferably, the poly-2-oxazoline homopolymer C segment comprises between 5-30 monomer units.

In one embodiment, a self-assembled particle comprising an amphiphilic polymer of the general Formula (I) as described above further comprises at least one amphiphilic polymer of Formula (II). In these and other embodiments, it is especially preferred that the self-assembled particle which comprises an amphiphilic polymer of Formula (II), comprise such a polymer wherein B is a polydimethylsiloxane and C is a poly-2-methyl-oxazoline.

In yet a further embodiment, the self-assembled particles independently comprise a therapeutic agent, a diagnostic agent or an oligonucleotide. In other words, the self-assembled particles incorporate, or are loaded with, a therapeutic agent, diagnostic agent, oligonucleotide or a combination thereof, which are physically independent, i.e. not covalently bonded to the self-assembled particles as such.

It is within the scope of the invention that various combinations of the amphiphilic polymers of Formula (I) and Formula (II) may be used to form self-assembled particles of the invention. Particularly preferred are self-assembled particles that are prepared from the following combinations of amphiphilic polymers:

(A1) An amphiphilic polymer of Formula (I) wherein Z is a terminal group, combined with an amphiphilic polymer of Formula (II) wherein Z is also a terminal group. The weight percentage of the Formula (I) polymer may range from about 1% to about 99%.

(B1) The combination of amphiphilic polymers (A1), as described above, further comprising an amphiphilic polymer of either Formula (I) or Formula (II) wherein Z is a linker conjugated to a ligand. The weight percentage of this further amphiphilic polymer conjugated with a ligand is preferably about 1% to 20%, relative to the total weight of the amphiphilic polymers.

(C1) The combination of amphiphilic polymers (A1), as described above, wherein the resulting self-assembled particle comprises a therapeutic agent and/or a diagnostic agent which is not covalently bonded to any of the amphiphilic polymers. The weight percentage of the therapeutic agent, relative to the total weight of the self-assembled particle composition is preferably about 1 to 50%. The weight percentage of the diagnostic agent, relative to the total weight of the self-assembled particle composition is preferably about 1 to 10%.

(D1) Combination B1 as described above, wherein the resulting self-assembled particle further comprises a therapeutic agent and/or a diagnostic agent which is not covalently bonded to any of the amphiphilic polymers. The weight percentage, relative to the total weight of the amphiphilic polymers, of the amphiphilic polymer conjugated with a ligand is preferably about 1% to 20%. The weight percentage of the therapeutic agent, relative to the total weight of the self-assembled particle composition is preferably about 1 to 50%. The weight percentage of the diagnostic agent, relative to the total weight of the self-assembled particle composition is preferably about 1 to 10%.

The self-assembled particles, as described in all of the above embodiments, are preferably selected from a micelle or a vesicle. Particularly preferred are micelles. Compared to vesicles, micelles may be more readily prepared and are found also to be more stable after drug encapsulation, in particular in the encapsulation of hydrophobic and/or low or poorly water soluble therapeutic agents.

A micelle may be understood to be a self-assembled particle comprising a hydrophobic interior and a hydrophilic exterior. An inverted micelle, i.e. with a hydrophilic interior and hydrophobic exterior may form in a hydrophobic solvent. At a given concentration in water as the bulk solvent (i.e. the critical micelle concentration, or CMC), the amphiphilic polymers of the invention will begin to aggregate and self-assemble to form a defined micelle structure. This process is reversible; below this concentration, the amphiphilic polymers become largely unassociated. While various shapes and geometric arrangements may be feasible (e.g. lamellae, cylinder), the micelles of the invention are preferably spheroidal or ellipsoidal.

A vesicle, as understood herein, is a self-assembled particle comprising a closed bilayer membrane structure, and an enclosed aqueous compartment. The outer, solvent-facing surface of the vesicle and the inner compartment-facing surface of the vesicle usually feature the hydrophilic segments of the amphiphilic polymers. The vesicle may be unilamellar, i.e. comprising one bilayer, or it may be multilamellar, i.e. comprising more than one bilayer membrane.

As mentioned, the micelles and vesicles of the invention are preferably substantially spheroidal in shape. The average diameter of such micelles is generally in the range of about 20 nm to about 150 nm. The average diameter of the vesicles formed from the amphiphilic polymers are generally in the range of 40 nm to 250 nm. Micelle size, shape and geometries may be determined by the usual characterization methods known in the art, for example by DLS or TEM analysis.

The micelles and vesicles may also be prepared by methods generally known in the art, including methods such as film hydration or nano-precipitation, which are described in further detail below in the Example section. In a further embodiment, the self-assembled particles are transformed into solid particles or nanoparticles by means of lyophilization or other methods generally known in the art for preparing solid particles from colloidal dispersions.

In another aspect, the invention relates to amphiphilic polymers of Formula (I) and their methods of preparation, that is, the amphiphilic polymers of the general Formula (I)

$$B\text{-}(L_0\text{-}A\text{-}Z)_n,$$

wherein n is 1, or 2 and B is a hydrophobic polysiloxane segment; and wherein $L_0$, Z, and A are as follows:

The divalent linker segment $L_0$ is represented by the formula: $R_8(Q)_u$ wherein $R_8$ is selected from an alkylene or arylene group containing 1 to 20 carbon atoms and an alkylene or arylene group containing 1 to 20 carbon atoms interrupted by one or more of the heteroatoms O, N, S; Q is selected from —O—, —S—, —S—S—, —NHC(O)—, —C(O)NH—, —OC(O)NH—, —NHC(O)O—, —OC(O)—, C(O)O—, —NHC(O)NH—, —SC(O)—, —C(O)S—, —NHC(S)NH—,

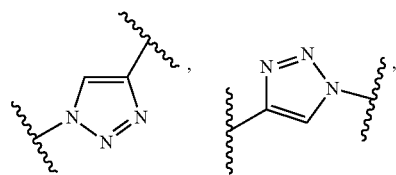

wherein $R_9$ is hydrogen or C1-C4 alkyl and u is 0, 1, or 2.

Z is a terminal group of formula $-X^1-Q_0$, wherein $X_1$ is selected from —O—, —S—, —NH—, —$NR_{10}$—,

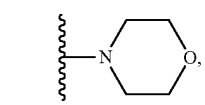

—$N_3$,

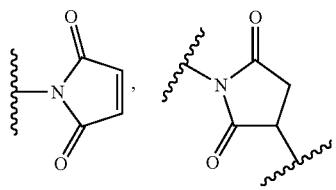

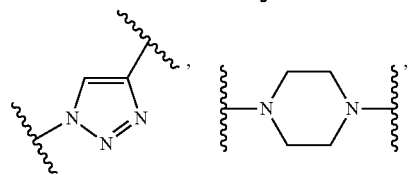

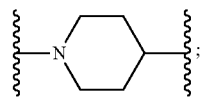

and $Q_0$ is absent or selected from H, unsubstituted or substituted alkyl, alkenyl, aralkyl, alkynyl, heterocyclyl or aryl, —C(O)—$(CH_2)_q$—COOH, —C(O)O—$R_{10}$, —$(CH_2)_q$—C(O)O—$R_{10}$, —C(O)$R_{10}$, —NHC(O)—$(CH_2)_q$—$N_3$, —$(CH_2)_q$—$N_3$, or —$SR_{10}$, wherein $R_{10}$ is selected from unsubstituted or substituted alkyl, alkenyl, aralkyl group and q is an integer from 1 to 10.

Alternatively, Z is a linker conjugated to a ligand of formula -$L_3$-$R_{11}$, wherein $L_3$ is selected from —S—, —O—, —OC(O)—, —OC(O)NH—, —NHC(O)—, —NHC(O)NH, —NHC(S)NH—, —NHC(O)O—,

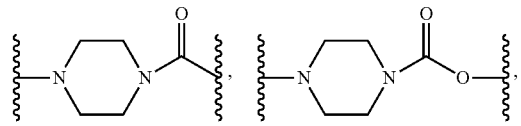

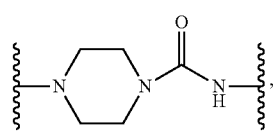

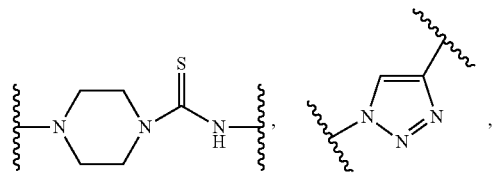

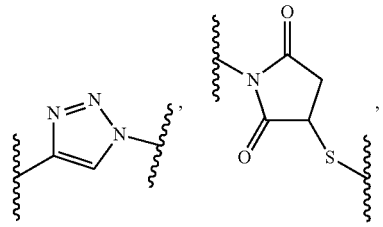

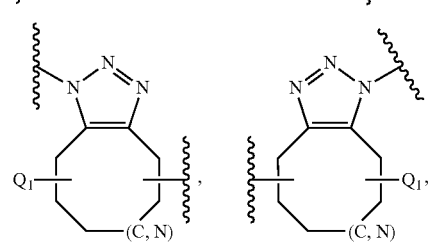

wherein $Q_1$ represents one or more substituents; and $R_{11}$ is a ligand selected from a small molecule, antibody, antigen-binding fragment (fab), single domain antibody, oligonucleotide, a carbohydrate, and in particular from folate, biotin or peptides.

The hydrophilic poly-2-oxazoline copolymer segment A is of Formula (I-a):

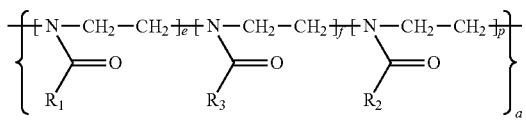

wherein $R_1$, $R_3$ are independently selected from a linker conjugated to a therapeutic, diagnostic or ligand; and a linker comprising a functional group selected from an amine, an azide, an alkyne, an aldehyde, an acetal, an alcohol, a carboxylic acid, an activated carboxylic acid, an oxyamine, a ketone, a ketal, an ester, a maleimide, a vinyl sulfone, an orthopyridyl disulfide or a chloroformate;

$R_2$ is independently selected from C1-C20 alkyl or aralkyl group;

e, f, are integers independently selected from 0-500, provided that e and f are not simultaneously selected as 0;

p is an integer selected from 2-500;

and a is selected from ran indicating a random copolymer wherein the units as defined by the integers e, f and p are in random or from block, indicating a block copolymer wherein the units as defined by the integers e, f, and p are sequential segments.

The hydrophobic polysiloxane B of such amphiphilic polymers is preferably a polysiloxane as described above of Formula (III) or a related compound.

In respect of the groups $R_1$ and $R_3$, these preferably comprise a linker conjugated to a therapeutic agent, a diagnostic agent or a ligand. In one embodiment, the linker comprises a covalent bond that is hydrolysable, i.e. that can be cleaved by hydrolysis, preferably under physiological conditions. In another embodiment, the linker comprises only non-hydrolysable covalent bonds. Alternatively, $R_1$ and $R_3$ may be a linker comprising a functional group which can be further chemically modified (i.e. under general reaction conditions with nucleophiles or electrophiles) and which allows for the attachment of, or linking to, another chemical entity such as a therapeutic or diagnostic agent or a ligand. In preferred embodiment, the $R_1$ and $R_3$ moieties comprise a functional group selected from an amine (which may be secondary, or tertiary or quaternary) and an azide.

$R_2$ on the other hand is preferably a chemically inert group, i.e. it does not readily undergo chemical reactions, for example during the chemical modification of $R_1$ or $R_3$, and also not with any of the potentially reactive functional groups of $R_1$ or $R_3$. $R_2$ is preferably a C1-C20 alkyl or aralkyl group; in particularly, $R_2$ may be a C1-C10 alkyl such as methyl or ethyl. In one embodiment, the amphiphilic polymer of Formula (I) as above comprises a poly-2-oxazoline copolymer segment A of Formula (I-b):

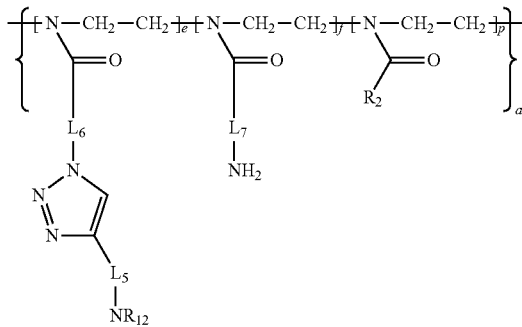

wherein $L_5$, $L_6$ and $L_7$ are independently selected from C1-C20 alkylene, C4-C12 arylene, and C1-C20 alkylene or C4-C12 arylene interrupted by one or more of the heteroatoms O, N, S;

$R_{12}$ is selected from —H(H), —(H)$R_{13}$, —($R_{13}$)$_2$ or —($R_{13}$)$_2R_{14}$X, wherein $R_{13}$, $R_{14}$ are independently selected from substituted or unsubstituted C1-C20 alkyl and substituted or unsubstituted aralkyl, and wherein X is a negative counterion.

In this particular embodiment, the amphiphilic polymer also comprises a terminal group Z selected from —OH, —NH$_2$,

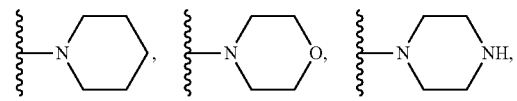

—OR$_{15}$, —NR$_{15}$R$_{16}$, and —SR$_{15}$, wherein R$_{15}$ and R$_{16}$ are independently selected from unsubstituted or substituted alkyl, alkenyl, and aralkyl.

Preferably, $L_6$ and $L_7$ are independently selected from C1-C20 alkyl, in particular from C3-C10 alkyl.

In a further embodiment, f is 0, so that A is a hydrophilic poly-2-oxazoline copolymer segment of Formula (I-c):

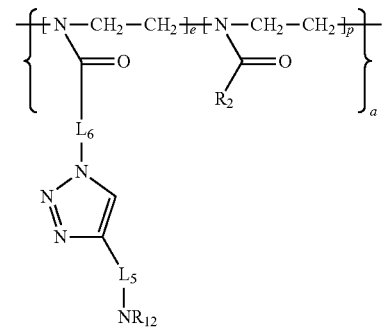

In this case, the poly-2-oxazoline copolymer is derived from two 2-oxazoline monomers.

Preferably, $R_2$ in Formula (I-b) or Formula (I-c) is a C1-C20 alkyl or aralkyl group; in particular, the $R_2$ substituent may be a C1-C10 alkyl such as methyl or ethyl. Also preferred are embodiments in which $L_5$ is a C1-C10 alkylene, in particular methylene, and where $R_{12}$ is —H(H), —(H)R$_{13}$, —(R$_{13}$)$_2$ or —(R$_{13}$)$_2$R$_{14}$X, where R$_{13}$, R$_{14}$ are independently selected from unsubstituted C1-C5 alkyl; in particular, methyl.

Further preferences for amphiphilic polymer comprising a hydrophilic segment of Formula (I-a), (I-b) or (I-c) include embodiments where e is selected as 0 and f is selected from the range of 1-20; or where f is selected as 0 and e is selected from the range of 1-20.

The amphiphilic polymers comprising a poly-2-oxazoline copolymer segment A of Formula (I-b) or Formula (I-c), and the self-assembled particles comprising and prepared from them are found to be, in particular, useful for gene delivery and gene therapy. In yet a further embodiment, the self-assembled particles comprising such amphiphilic polymers further comprise of a gene or gene fragment or derivatives (e.g. DNA, plasmids, siRNA, etc.). The pendant amino functional groups in such amphiphilic polymers can become positively charged under normal physiological conditions, which is useful for the incorporation of the genetic material.

In yet another embodiment, the amphiphilic polymer of Formula (I) as described above comprises a hydrophilic poly-2-oxazoline copolymer segment A of Formula (I-d):

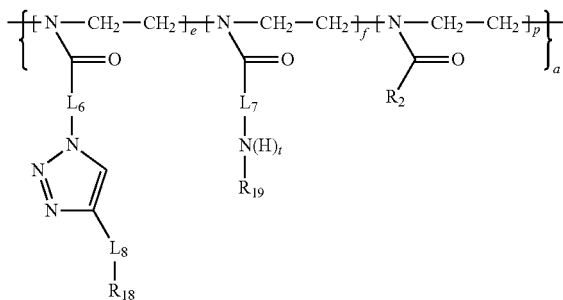

wherein $R_{18}$ and $R_{19}$ are independently selected for each monomeric unit from a diagnostic agent, a therapeutic agent, a ligand, and a substituent preferably selected from hydrogen, C1-C20 alkylene, and C1-C20 arylene; provided that for at least one monomeric unit, $R_{18}$ and/or $R_{19}$ is a diagnostic agent, a therapeutic agent or a ligand;

$L_6$ and $L_7$ are independently selected from C1-C20 alkylene, C4-C12 arylene, and C1-C20 alkylene or C4-C12 arylene interrupted by one or more of the heteroatoms O, N, S;

$L_8$ is a divalent linker of formula $—R_{20}(Y)_s$, wherein $R_{20}$ is a C1-C20 alkylene or arylene, or a C1-C20 alkylene or arylene group interrupted by one or more of heteroatoms O, N, S; Y is —S—S—, —NHC(O)—, —C(O)NH—, —OC(O)NH—, —NHC(O)O—, —OC(O)—, —OC(O)O—, —C(O)O—, —NHC(O)NH—, —SC(O)—, —C(O)S—, —NHC(S)NH—, —NH— and —C(O)—NH—N=, and s is 0, 1 or 2;

t is selected from an integer of 0 or 1;

and wherein Z is a terminal group selected from —OH, —NH₂,

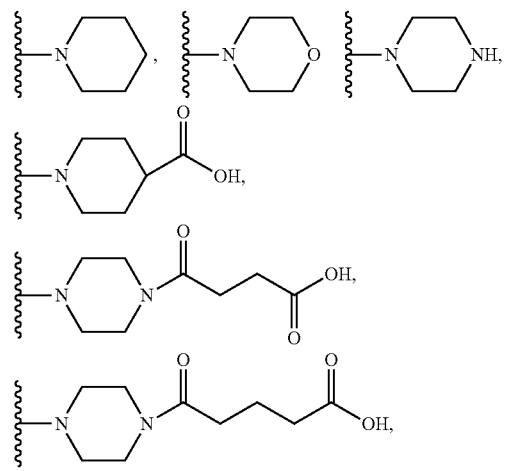

—$OR_{16}$, —$NR_{16}R_{17}$, —$SR_{16}$, wherein $R_{16}$ and $R_{17}$ are independently selected from unsubstituted or substituted alkyl, alkenyl, or aralkyl.

It should be understood that the phrase referring to the independent selection for $R_{18}$ and $R_{19}$ for each monomeric unit refers also to the independent selection for each of the $R_{18}$ and $R_{19}$ moieties, of a diagnostic agent, a therapeutic agent, a ligand or a substituent. The $R_{18}$ and $R_{19}$ moieties of the monomer units are substituents other than a ligand, diagnostic agent or therapeutic agent, particularly preferred substituents being hydrogen (H), C1-C20 alkylene or C1-C20 arylene.

In a preferred embodiment however, all of the monomeric units defined by integer e and/or f may comprise of one or more diagnostic agent, therapeutic agent, ligand or combinations thereof. In a further embodiment of Formula (I-d), f is 0, so that A is a hydrophilic poly-2-oxazoline copolymer segment of Formula (I-e):

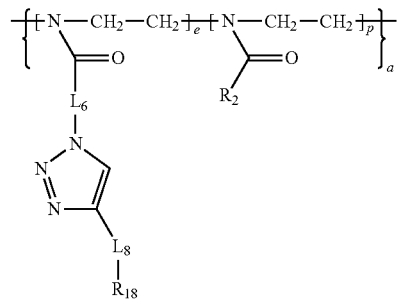

wherein $R_{18}$ is independently selected for each monomeric unit from a therapeutic agent or a diagnostic agent or a substituent other than a therapeutic agent or a diagnostic agent, provided that for at least one monomeric unit, $R_{18}$ is a diagnostic agent, a therapeutic agent or a ligand. The substituent is preferably selected from hydrogen, C1-C20 alkylene, and C1-C20 arylene. The therapeutic agent is preferably selected from a chemotherapeutic and antineoplastic agent such as doxorubicine or taxol. The diagnostic agent is preferably selected from a fluorescent dye, a radiolabel, a PET-imaging agent, an MRI-imaging agent and a sensitizer. In one embodiment, the diagnostic agent is selected from photoacoustic imaging agents.

In general, the covalent attachment or conjugation of a therapeutic agent such as a drug to the amphiphilic polymers of the invention is accomplished by reaction of an active chemical group on the polymer portion with a complementary chemical functional group on the therapeutic agent. In one option, the covalent attachment occurs at the linker portion (i.e. $L_8$). Preferably, $L_8$ comprises a hydrolysable bond, which is often useful for in vivo drug release. Preferred hydrolysable bonds include ester, carbamate, amide, urea and thiourea bonds.

In yet a further embodiment of Formula (I-d), e is 0, so that A is a hydrophilic poly-2-oxazoline copolymer segment of Formula (I-f):

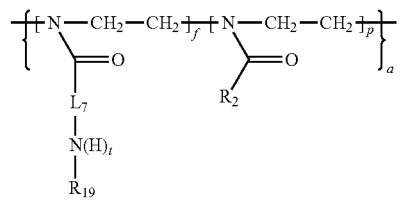

wherein $R_{19}$ is independently selected for each monomeric unit from a therapeutic agent, a diagnostic agent or a substituent preferably selected from hydrogen, C1-C20 alkylene, and C1-C20 arylene, provided that for at least one monomeric unit, $R_{19}$ is a diagnostic agent, a therapeutic agent or a ligand. The therapeutic agent is preferably selected from a chemotherapeutic or antineoplastic agent such as doxorubicine or taxol. The diagnostic agent is preferably selected from a fluorescent dye, a radiolabel, a PET-imaging agent, an MRI-imaging agent and a sensitizer., In one embodiment, the diagnostic agent is selected from photoacoustic imaging agents.

The copolymer segment of Formula (I-d) or (I-e) for example may comprise monomer units wherein the moiety $R_{18}$ is a diagnostic agent and also monomer units wherein the moiety $R_{18}$ is a therapeutic agent. Likewise, the copolymer segment of Formula (I-d) or (I-f) may also comprise monomeric units wherein the moiety $R_{19}$ is a diagnostic agent and also monomeric units wherein $R_{19}$ is a therapeutic agent. In other embodiments of the copolymer segment of Formula (I-d), the monomeric units defined by the integer e may comprise monomeric units wherein $R_{18}$ is a therapeutic agent, and monomeric units defined by the integer f comprising monomeric units wherein $R_{19}$ is a substituent other than a diagnostic agent or therapeutic agent, or wherein $R_{19}$ is a diagnostic agent. In another example, the copolymer segment of Formula (I-d) or (I-e) may comprise monomer units defined by the integer e wherein $R_{18}$ is one therapeutic agent as well as monomer units wherein $R_{18}$ is a second therapeutic agent.

Preferably, $L_6$ of Formula (I-d) and $L_7$ of Formula (I-f) are selected from C1-C20 alkyl, in particular from C3-C10 alkyl. The amphiphilic polymers of Formula (I) may be prepared according to two general methods. In one method, the hydrophilic poly-2-oxazoline copolymer segment A and the hydrophobic polysiloxane segment B are independently prepared, and then linked together by a reaction between two active functional groups on the respective terminal ends of the polymers. In an example of this method, the hydrophilic poly-2-oxazoline copolymer comprises an azide functional group at a terminal end, while the polysiloxane segment B comprises an alkynyl functional group at a terminal end (or vice versa); segment A and B are linked via a 1,3-dipolar cycloaddition reaction (also known as an azide-alkyne 1,3-dipolar or [3+2] cycloaddition or as a 'click' reaction).

In the second general method of preparing an amphiphilic polymer of Formula (I), either a hydrophilic segment A or hydrophobic segment B is independently prepared and modified so as to serve as a suitable precursor and initiator in the polymerization of the second segment.

In one embodiment of the invention, an amphiphilic polymer of Formula (I) is prepared from a hydrophobic segment B that is functionalized at one or both terminal ends of the polymer chain with an initiator group such as —Br, —I, -OMs (—O—SO$_2$CH$_3$, mesylate), —OTs (—O—SO$_2$—C$_6$H$_4$-p-CH$_3$, or tosylate), —OTf (—O—SO$_2$—CF$_3$, triflate). The most preferred initiator group is the triflate. The poly-2-oxazoline polymer segment(s) A are then prepared from this precursor, also referred to herein as a macroinitiator, by means of a living cationic polymerization process. Such a process comprises the steps of initiation and chain propagation by the addition of a 2-oxazoline monomer to the macroinitiator, and a step of termination, such as by the addition of a nucleophilic reagent (for example, a hydroxide, piperazine, or azide, etc.). A catalyst may be added to promote the polymerization process.

These methods may also be applied to the synthesis of an amphiphilic polymer of the general Formula (II).

This polymerization process is preferably carried out in substantially inert solvents such as, hexane, toluene, benzene, chloroform, or polar aprotic solvents such as, ethyl acetate, acetonitril, DMF, DMSO, dichloromethane, or mixtures thereof. Preferred solvents for the polymerization are chloroform and acetonitrile.

As mentioned above, the polymerization process to form the poly-2-oxazoline polymer segment may be carried out in several ways. In one embodiment, a mixture of two or more appropriate 2-oxazoline monomers is reacted with the hydrophobic polysiloxane macro-initiator to yield a random copolymer segment. In another embodiment, the poly-2-oxazoline segment A can be synthesized in blocks by initiating polymerization with an appropriate polysiloxane initiator with a first 2-oxazoline monomer, followed by addition of a second 2-oxazoline monomer when the polymerization of the first block is completed. The addition of the second 2-oxazoline monomer reinitiates the polymerization with the living cation at the terminus of the polymer chain. The reaction conditions may differ for each step. In both processes, the polymerization process is terminated by addition of a nucleophilic reagent.

In a preferred embodiment, the invention provides a method of preparing an amphiphilic polymer of Formula (I) comprising a step of cationic ring-opening polymerization of a polysiloxane initiator with at least one 2-(azidoalkyl)-2-oxazoline monomer and at least one 2-alkyl-2-oxazoline or 2-aralkyl-2-oxazoline monomer. In particular, the amphiphilic polymers comprising a hydrophilic poly-2-oxazoline copolymer segment A of the present invention may be prepared by copolymerization of at least two 2-substituted-2-oxazlines, preferably an 2-(azidoalkyl)-2-oxazoline and an 2-alkyl-2-oxazoline or 2-aralkyl-2-oxazoline monomer, using a triflate-functionalized hydrophobic polydimethylsiloxane segment B as a microinitiator.

The amphiphilic polymers resulting from these polymerization processes are highly versatile in respect of further functionalization. This provides, in turn, an easy and modular approach for the preparation of the self-assembled particles of the invention, and for tuning their properties. For example, the poly-2-oxazoline segments may be modified, for example, the addition of linkers and/or an active agent such as a diagnostic agent, ligand, or therapeutic agent.

The methods of preparing an amphiphilic polymer of Formula (I) as described above may further comprise a step of azide reduction and/or a step of 1,3 dipolar cycloaddition with an alkynyl compound.

In general, an amphiphilic polymer comprising an azide functional group may be used as a precursor to an amphiphilic polymer with an amino functional group. While it is contemplated that any azide reduction reaction or reaction conditions known in the art may be used for this purpose, methods which are mild and which are compatible with the structural elements of the amphiphilic polymer (especially the acid-labile polysiloxane segment) are preferred. Thiols have been found to be particularly suitable reagents for reducing azide functional groups in the amphiphilic polymers of the invention.

The azide functionality may also be used as a partner for a 1,3 dipolar cycloaddition with an entity comprising an alkynyl functional group. The resulting triazole adduct may serve as a selective means for covalently linking the amphiphilic polymer to, for example, an active pharmaceutical agent, or a ligand. Reaction conditions for these reactions are typically mild, and thus particularly amenable for selective coupling of the amphiphilic polymer to compounds and molecules comprising with sensitive or reactive functionality. In one embodiment, the 1,3-dipolar cycloaddition reaction is copper-catalysed. The catalyst may be selected from a Cu+, Cu++, such as CuI, CuBr, CuSO$_4$.5H$_2$O, copper complexes. Useful additives for these reaction include, but are not limited to, sodium ascorbate, triethylamine, DIPEA, TBTA (Tris[(1-benzyl-1H-1,2,3-triazol-4-yl)methyl]amine), PMEDTA (N,N,N',N'',N''-pentamethyldiethylenetriamine).

It has been found by the inventors that the introduction of azide via a 2-oxazoline monomer comprising such functionality as described above into the copolymerization process provides a versatile handle for the further functionalization and diversification of the amphiphilic polymers of the general Formula (I), B-(L$_0$-A-Z)$_n$. The azido functional group of such amphiphilic polymers may be subject to reduction and/or 1,3-dipolar cycloaddition reactions as described above. For instance, and as exemplified in Example 8 below, subjecting an amphiphilic polymer comprising a segment of Formula (I-d) to a process comprising first a step of 1,3-dipolar cycloaddition, then a step of azide reduction provides an amphiphilic polymer adduct comprising both triazole and amino functional groups.

Further, the amphiphilic polymers of the general Formula (I) as described above comprising a poly-2-oxazoline copolymer segment A of Formula (I-b) or Formula (I-c) may be prepared from a precursor amphiphilic polymer comprising a poly-2-oxazoline copolymer segment A of Formula (I-g):

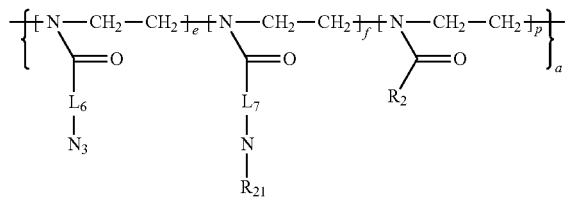

wherein

L$_6$ and L$_7$ are independently selected from C1-C20 alkylene, C4-C12 arylene, and C1-C20 alkylene or C4-C12 arylene interrupted by the heteroatoms O, N, S;

and R$_{21}$ is selected from H(H), H(R$_{22}$), (R$_{22}$)$_2$ and (R$_{22}$)$_2$R$_{23}$X, wherein R$_{22}$ and R$_{23}$ are independently selected from substituted or unsubstituted C1-C20 alkyl and substituted or unsubstituted aralkyl, and wherein X is a negative counterion.

In a particular embodiment, f is 0 such that the amphiphilic polymer comprises a hydrophilic poly-2-oxazoline copolymer segment of Formula (I-h):

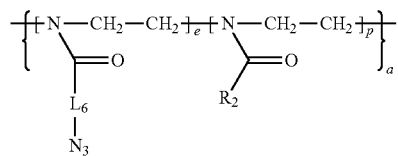

and wherein Z is a terminal group selected from —OH, —N$_3$, —NH$_2$,

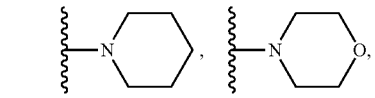

—OR$_{16}$, —NR$_{16}$R$_{17}$, —SR$_{16}$,

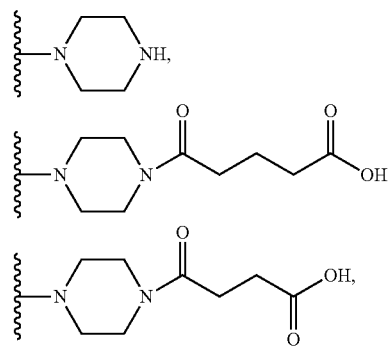

wherein R$_{16}$ and R$_{17}$ are independently selected from unsubstituted or substituted alkyl, alkenyl, and aralkyl.

The azide functionality of this amphiphilic polymer can function as a direct means for covalently attaching a therapeutic agent to the amphiphilic polymers of the invention, to provide, for example, an amphiphilic polymer comprising a hydrophilic poly-2-oxazoline copolymer segment A of Formula (I-e). In such cases, a therapeutic agent modified to comprise an containing alkynyl functional group can be conjugated directly to the amphiphilic polymer via a 1,3 dipolar cycloaddition click reaction.

In yet further embodiment of an amphiphilic polymer comprising a poly-2-oxazoline copolymer segment A of Formula (I-g), e is 0 and R$_{21}$ is H(H), such that A is a hydrophilic poly-2-oxazoline copolymer segment of Formula (I-i)

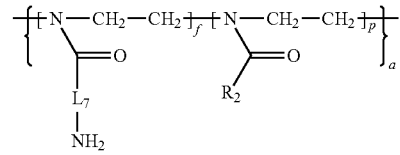

and wherein Z is a terminal group selected from —OH, —N$_3$, —NH$_2$,

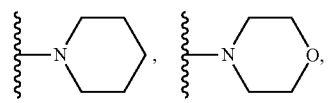

—OR$_{16}$, —NR$_{16}$R$_{17}$, —SR$_{16}$,

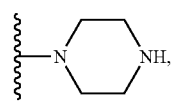

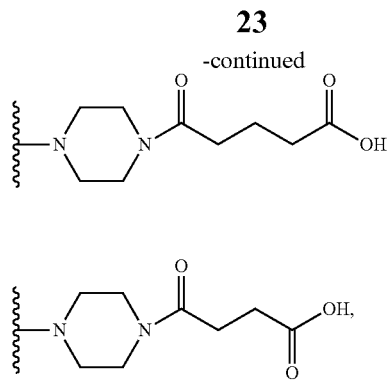

wherein $R_{16}$ and $R_{17}$ are independently selected from unsubstituted or substituted alkyl, alkenyl, and aralkyl.

The pendant free primary amine of amphiphilic polymers comprising a segment of Formula (I-i) may be used as a nucleophile in coupling reactions with diagnostic or photodynamic therapy agents. Commercial agents that are suitable for coupling and which do not require chemical modification may be directly used (e.g. fluorescein isocynate (FITC), rhodamine isocyanate), alternatively the diagnostic or photodynamic therapy can be chemically modified so as to provide a means for coupling with the pendant primary amine moiety of the amphiphilic polymer.

As mentioned above, the amphiphilic polymers of the invention may comprise a group Z at a terminal end of the polymer. When the terminal group is selected as —OH, —NH$_2$ or as a secondary amine, these may be further used as a nucleophilic partner in a reagent-assisted coupling reaction with a ligand. Alternatively, where the terminal group is an azide, a ligand modified to comprise an alkynyl functional group may be conjugated to the amphiphilic polymer terminal end via a 1,3 dipolar cycloaddition click reaction.

Further embodiments, options, and/or preferences are illustrated by the following examples and figures.

EXAMPLES

Amphiphilic Polymer Synthesis

Example 1

Preparation of 2-(4-azidobutyl)-oxazoline (1)

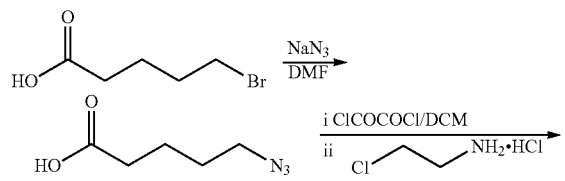

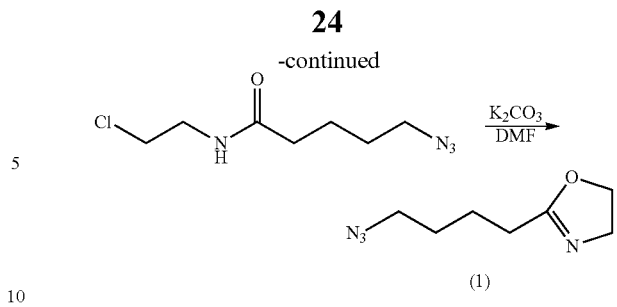

To a solution of 5-bromopentanoic acid (5.7 g, 32 mmol) in DMF (40 ml) was added solid sodium azide (3.0 g, 48 mmol). The reaction mixture was heated to 70° C. and stirred for 12 h at same temperature. Solvent was removed under high vacuum to afford a residue. The residue was diluted with dichloromethane and washed with 0.1NHCl. The aqueous phase was extracted with dichloromethane twice. The combined organic phases were washed with brine, dried over Na$_2$SO$_4$ and concentration to afford 2.75 g 5-azidopentanoic acid as a yellow oil. Yield: 61% $^1$HNMR (400 MHz, CDCl$_3$): δ 9.30(br, 1H), 3.29(t, 2H, J=6.5 Hz), 2.37(t, 2H, J=7.1 Hz), 1.66(m, 4H) ppm.

A solution of 5-azidopentanoic acid (2.75 g, 19.2 mmol) and trace amount of anhydrous DMF in dichloromethane (40 ml) was cooled to 0° C.-4° C. in an ice batch under argon. Then a solution of oxalyl chloride (4.84 g, 38.4 mmol) in dry dichloromethane (10 ml) was added dropwise. The reaction mixture was stirred at same temperature for 1 h. Another solution of 2-chloroethyl-amine hydrochloride (6.68 g, 57.6 mmol) in dry pyridine (10 ml) was added. After addition, the cooling batch was removed. The mixture was transferred to a separatory funnel and washed with 10% aqueous HCl and water respectively. The organic phase was dried over Na$_2$SO$_4$ and concentrated by evaporation to yield 1.95 g 5-azido-N-(2-chloroethyl)pentan-amide as a yellow oil. Yield: 50% $^1$HNMR (400 MHz, CDCl$_3$) δ 5.95(br, 1H), 3.60(m, 4H), 3.30(t, 2H, J=6.5 Hz), 2.25(t, 2H, J=7.4 Hz), 1.73(m, 2H), 1.65(m, 2H) ppm.

To a solution of 5-azido-N-(2-chloroethyl)pentanamide (1.9 g, 9.3 mmol) in dry DMF (20 ml) was added solid potassium carbonate (2.56 g, 18.6 mmol). The reaction mixture was stirred at 55° C. for 30 h. Solvent was removed by evaporation to afford a residue. The residue was dissolved in ethyl acetate and filtrated and solid was washed with ethyl acetate for several times. The combined organic phases were evaporated and dried under high vacuum overnight to give 1.55 g of compound (1) as a slightly yellow oil. Yield: 99%. $^1$HNMR (400 MHz, CDCl$_3$) δ 4.25(t, 2H, J=9.4 Hz), 3.83(t, 2H, J=9.4 Hz), 3.30(t, 2H, J=6.4 Hz), 2.33(t, 2H, J=7.2 Hz), 1.71(m, 2H), 1.66(m, 2H) ppm.

Example 2

Preparation of

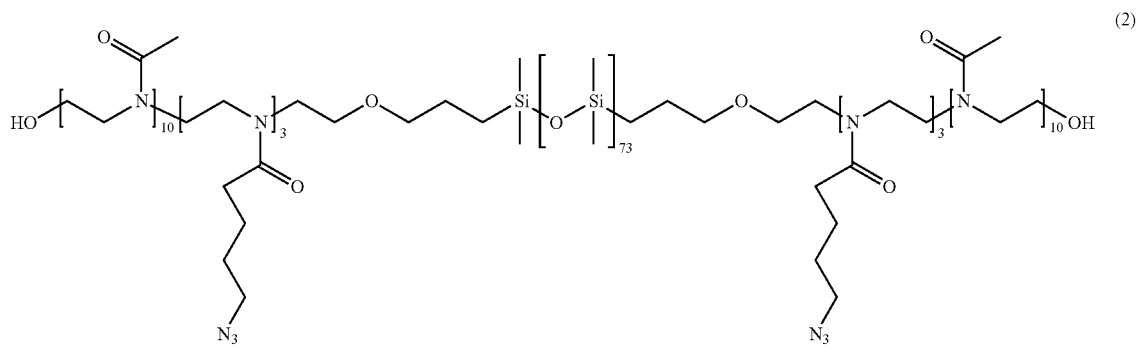

To solution of Poly(dimethylsiloxane), bis(hydroxyalkyl) terminated (5.6 g, 1 mmol) in toluene (25 mL) was added 2,6-lutidine (0.35 mL, 3 mmol), followed by addition of a solution of trifluoromethanesulfonic anhydride (0.4 mL, 2.4 mmol) in hexane (2.5 mL) dropwise in ice bath under argon. The reaction mixture was stirred at same temperature for 3 h. Then solvent was removed under vacuum to give an active intermediate as a yellow oil. The oil was dissolved in a mixed solvent of chloroform (15 mL) and acetonitrile (20 mL). A first monomer, 2-(4-azidobutyl)-oxazole (1.03 g, 6.1 mmol) was added at r.t. The reaction mixture was heated and stirred at 60° C. for 43 h. Then it was cooled to r.t. and the second monomer 2-methyl-oxazoline (1.7 mL, 20 mmol) was added. The reaction mixture was heated to 60° C. again and stirred at the same temperature for 48 h, then quenched with a solution of triethylamine in water at r.t. Solvent was removed by evaporation to afford a residue. The residue was purified by ultra-filtration with cellulose regenerated membrane (a cut off at 5000 dalton) using ethanol/water (80:20, v/v, at least for four times. In the first time, a 5 ml of saturated $NaHCO_3$ solution was added) as eluent to produce 6.5 g compound (2) as a slightly yellow solid. Yield: 78%, 1HNMR (400 MHz, CDCl3) δ 3.30-3.75(m, 128H), 2.30-2.50(m, 12H), 2.05-2.21(m, 60H), 1.50-1.75(m, 28H), 0.50 (m, 4H), 0.02-0.09(m, 444H)ppm.

Example 3

Preparation of

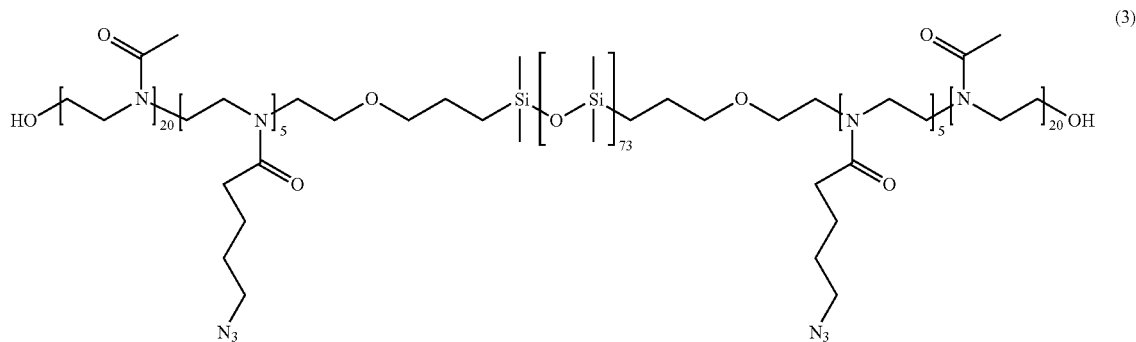

Compound (3) was prepared in analogy to the synthesis of compound (2). Yield 75%. $^1$HNMR (400 MHz, CD$_3$OD) δ 3.40-3.75(m, 212H), 3.37(m, 24H), 2.30-2.57(m, 20H), 2.05-2.19(m, 120H), 1.58-1.75(m, 44H), 0.56(m, 4H), 0.03-0.17(m, 444H)ppm.

Example 4

Preparation of

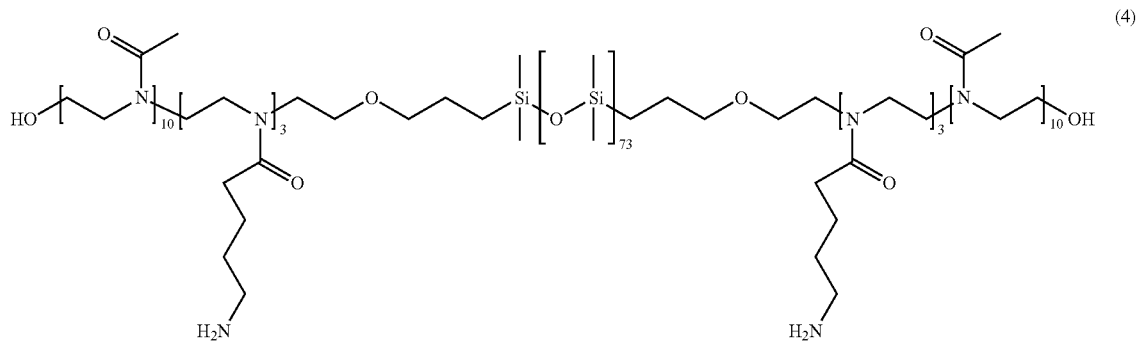

To a solution of compound (2) (840 mg, 0.1 mmol) in methanol (5 mL) was added triethylamine (0.56 mg, 4.0 mmol) at r.t., followed by addition of 1, 3-propandithiol (0.40 mL, 4.0 mmol). The reaction mixture was stirred at r.t. for 12 h. Solvent was removed under vacuum to afford a residue. The residue was purified by ultra-filtration with cellulose regenerated membrane (a cut off at 5000 dalton) using ethanol/water (80:20, v/v, at least for four times) as eluent to produce 560 mg compound (2) as a slightly yellow solid. Yield: 67%. $^1$HNMR (400 MHz, CD$_3$OD) δ 3.38-3.79 (m, 116H), 2.68(m, 12H), 2.30-2.53(m, 12H), 2.05-2.15(m, 60H), 1.45-1.70(m, 28H), 0.57(m, 4H), 0.03-0.17(m, 444H) ppm.

Example 5

Preparation of

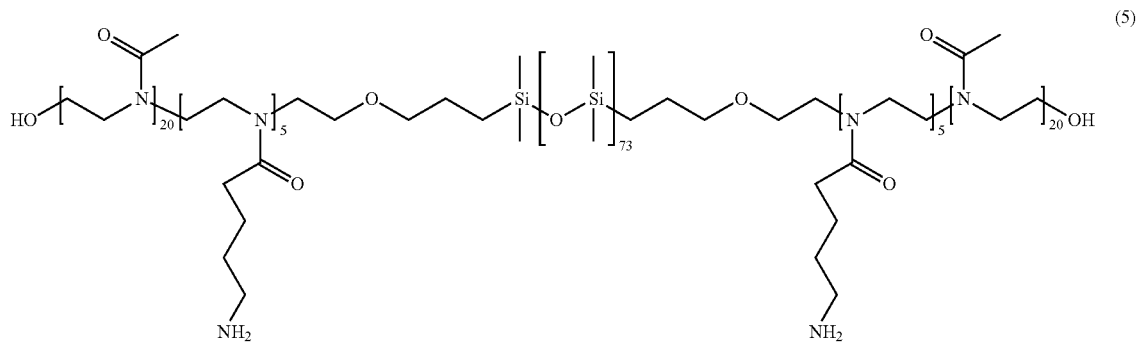

Compound (5) was prepared from compound (3), in analogy to the preparation of compound (4). Yield: 70%. $^1$HNMR (400 MHz, CD$_3$OD) δ 3.38-3.75(m, 212H), 2.68 (m, 20H), 2.30-2.53(m, 20H), 2.05-2.15(m, 120H), 1.45-1.70(m, 44H), 0.57(m, 4H), 0.03-0.17(m, 444H) ppm.

Example 6

Preparation of

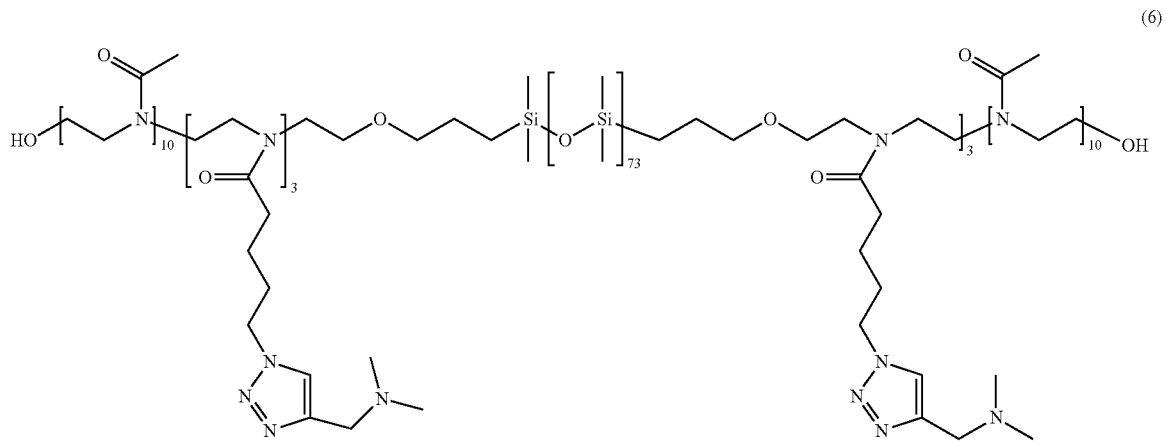

(6)

To a solution of compound (2) (840 mg, 0.1 mmol) in THF (6 mL, degassed with argon prior to use) was added 3-dimethylamino-1-propyne (83 mg, 1.0 mL) at r.t. The mixture was stirred for 5 min at the same temperature. An aqueous sodium-L-ascorbate (15 mg, 0.08 mmol) solution (0.5 mL) was added, followed by addition of aqueous $CuSO_4.5H_2O$ (7.5 mg, 0.03 mmol) solution (0.5 mL). The reaction mixture was stirred at r.t. for 24 h. Solvent was removed by evaporation to afford a residue. The residue was purified by ultra-filtration with cellulose regenerated membrane (a cut off at 5000 dalton) using ethanol/water (80:20, v/v, at least for four times) as eluent to produce 780 mg compound (2) as a slightly yellow solid. Yield: 88%. $^1$HNMR (400 MHz, $CD_3OD$) δ 7.93(m, 6H), 4.45(m, 12H), 3.38-3.75(m, 128H), 2.30-2.53(m, 12H), 2.27(s, 36H), 2.05-2.15(m, 60H), 1.95(m, 12H), 1.59(m, 16H), 0.59(m, 4H), 0.05-0.11 (m, 444H) ppm.

Example 7

Preparation of

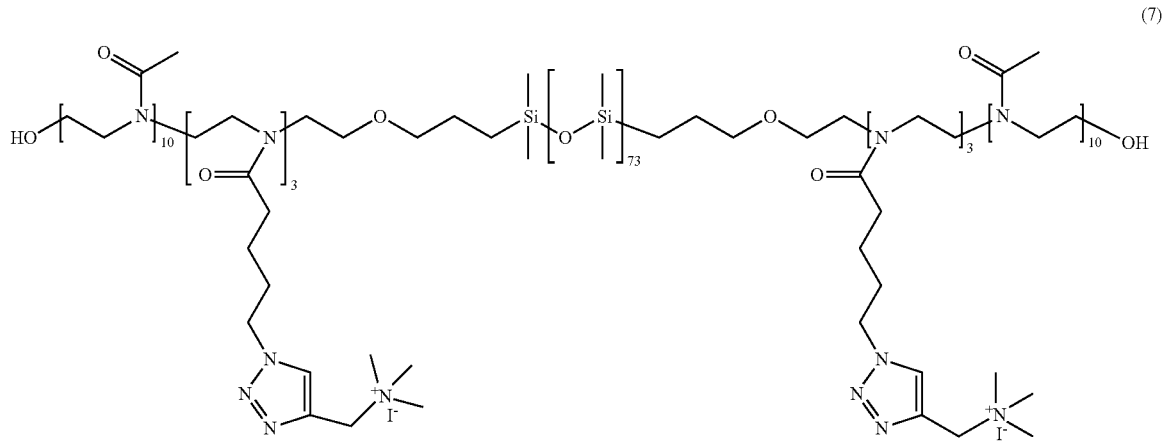

(7)

To a solution of compound (6) (100 mg, 0.011 mmol) in THF (2 mL) was added methyl iodide (14.2 mg, 0.10 mmol) under argon at r.t. The mixture was stirred at r.t. for 12 h. Solvent was removed by evaporation to afford a residue. The residue was washed with hexane twice. Then it was dried under high vacuum to give 110 mg compound (7) as a yellow solid. Yield 100%. $^1$HNMR(400 MHz, CD$_3$OD) δ 8.30-8.50(m, 6H), 4.50-4.80(m, 24H), 3.38-3.75(m, 116H), 2.94-3.20(m, 54H), 2.40-2.60(s, 12H), 2.05-2.18(m, 60H), 2.00(m, 12H), 1.60(m, 16H), 0.56(m, 4H), 0.05-0.11(m, 444H)ppm.

Example 8

Preparation of

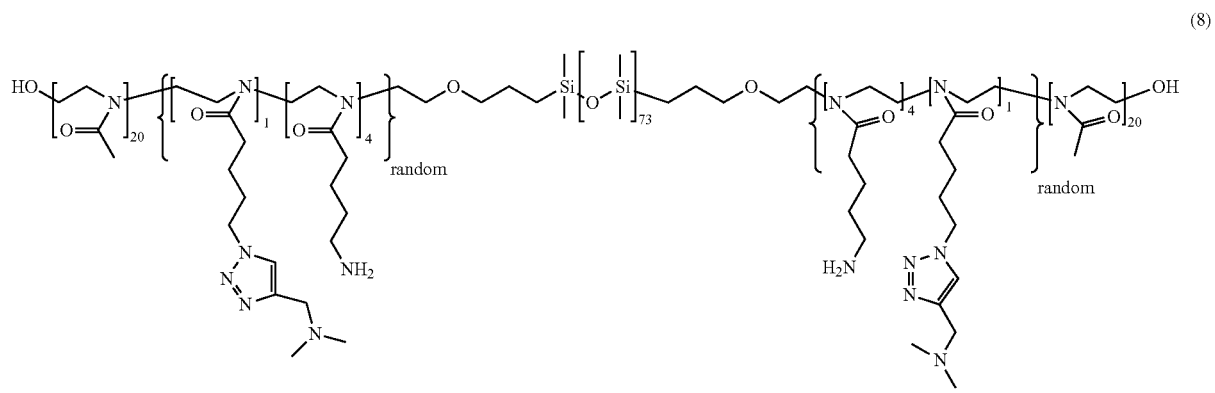

(8)

To a solution of polymer (3) (550 mg, 0.05 mmol) in THF (4 mL), which was degassed under argon for 20 min in advance, was added a solution of 3-dimethylamino-1-propyne (11.4 mg, 0.13 mmol) in t-BuOH (0.3 mL) at r.t., followed by addition of aqueous sodium L-ascorbate (5.4 mg, 0.027 mmol) solution (0.25 mL) and aqueous CuSO$_4$.5H$_2$O (3.4 mg, 0.014 mmol) solution (0.25 mL) successively. The resulted mixture was stirred at r.t. for 24 h. Then solvent was removed by evaporation to afford a residue. The residue was purified by ultra-filtration with cellulose regenerated membrane (a cut off at 5000 dalton) using ethanol/water (80:20, v/v, at least for four times) as eluent to produce 500 mg of intermediate as a slightly yellow solid. Yield: 88%.

The intermediate was dissolved in MeOH (3 mL) at rt, TEA (0.2 mL, 1.44 mmol) and 1, 3-propandithiol (0.15, 1.44 mmol) were added successively. The resulting mixture was stirred overnight. Solvent was removed by evaporation to afford a residue. The residue was purified by ultra-filtration with cellulose regenerated membrane (a cut off at 5000 dalton) using ethanol/water (80:20, v/v, at least for four times) as eluent to produce 445 mg compound (8) as a slightly yellow solid. Yield: 89%. $^1$HNMR(400 MHz, CD$_3$OD) δ 7.93(m, 2H), 4.43(m, 4H), 3.40-3.70(m, 216H), 2.60-2.80(m, 16H), 2.30-2.55(m, 20H), 2.25(s, 12H), 2.05-2.18(m, 120H), 1.90-2.00(m, 4H), 1.50-1.70(m, 40H), 0.59 (m, 4H), 0.05-0.15(m, 444H)ppm.

Example 9

Preparation of

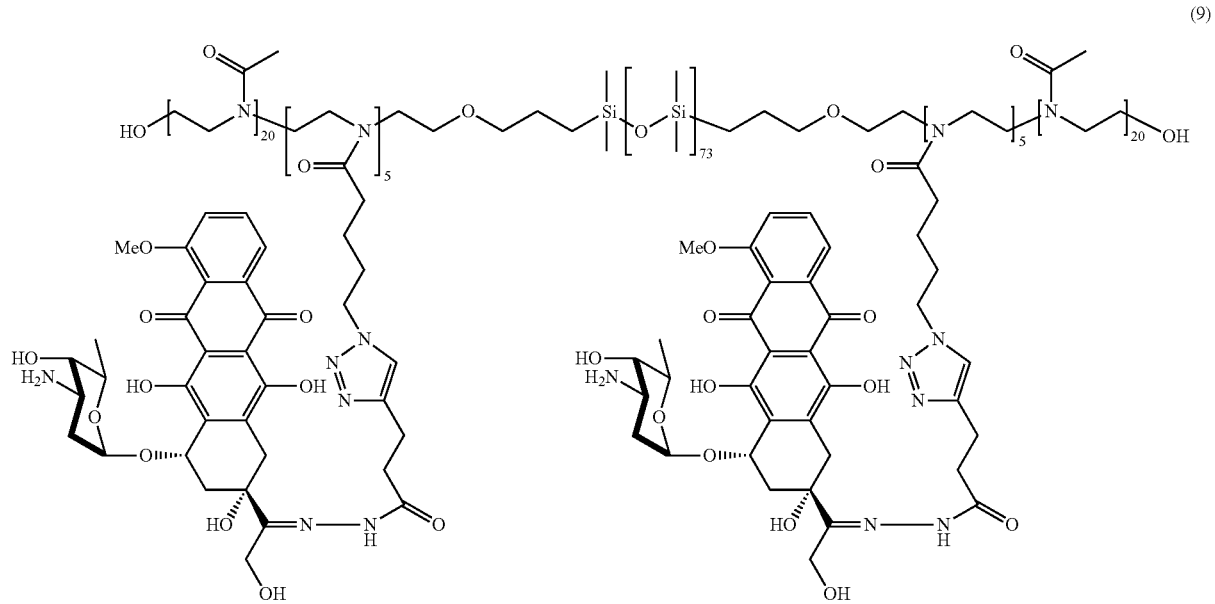

(9)

To a solution of polymer (3) (550 mg, 0.05 mmol) in THF (degassed, 4 mL) was added a solution of methyl pent-4-ynoate (84 mg, 0.75 mg) in t-BuOH (0.5 mL). The reaction mixture was stirred at r.t. for 5 min. An aqueous sodium L-ascorbate (7.5 mg, 0.04 mmol) solution (0.25 mL) and an aqueous $CuSO_4 \cdot 5H_2O$ (3.75 mg, 0.015 mmol) were added successively. The resulted mixture was stirred at r.t. for 12 h. Solvent was removed by evaporation to produce a residue. The residue was purified by ultra-filtration with cellulose regenerated membrane (a cut off at 5000 dalton) using ethanol/water (80:20, v/v, at least for four times) as eluent to produce 430 mg intermediate as a slightly yellow solid. Yield: 71%. $^1$HNMR(400 MHz, $CD_3OD$) δ 7.78(m, 10H), 4.38(m, 20H), 3.64(s, 30H), 3.40-3.70(m, 212H), 2.97(m, 20H), 2.70(m, 20H), 2.30-2.55(m, 20H), 2.05-2.18(m, 120H), 1.91 (m, 20H), 1.57(m, 24H), 0.54(m, 4H), 0.05-0.15(m, 444H)ppm.

To a solution of intermediate polymer (430 mg, 0.036 mmol) in ethanol (5 mL) was added aqueous $NH_2NH_2 \cdot H_2O$ (50-60%, 1 mL) at r.t. The reaction mixture was heated to reflux and continued to stir for 12 h. After that, the reaction was cooled down to r.t., which can be directly purified by ultra-filtration using ethanol/water (80:20, v/v, at least for four times) as eluent to produce 310 mg hydrazine intermediate as a slightly yellow solid. Yield 71%. $^1$HNMR(400 MHz, $CD_3OD$) δ 7.75(m, 10H), 4.37(m, 20H), 3.40-3.70(m, 212H), 2.98(t, 20H, J=7.60 Hz), 2.50(t, 20H, J=7.60 Hz), 2.30-2.60(m, 20H), 2.05-2.18(m, 120H), 1.90 (m, 20H), 1.54(m, 24H), 0.56(m, 4H), 0.05-0.14(m, 444H)ppm.

To a solution of hydrazine intermediate (50 mg) in methanol (1.5 mL) was added solid doxorubicin (12 mg) at r.t. under argon. The reaction mixture was stirred for 2 min. Then a catalytic amount of TFA was added. The reaction mixture was stirred at r.t. for 48 h. Solvent was removed by evaporation to afford a residue. The residue was dissolved in ethanol (10 mL) and the solution was centrifuged. Supernatant was collected and filtrated through a PPT (φ=0.45 μm) filter to remove unreacted doxorubicin. The combined organic solvent was concentrated under vacuum to afford 30 mg polymer-DOX compound (9) as a dark red solid. The loading amount of doxorubicin (weight of DOX/weight of polymer) is around 24%, as defined by UV spectrum measurements and calculation according to standard curve of UV absorption of DOX.

Example 10

Preparation of

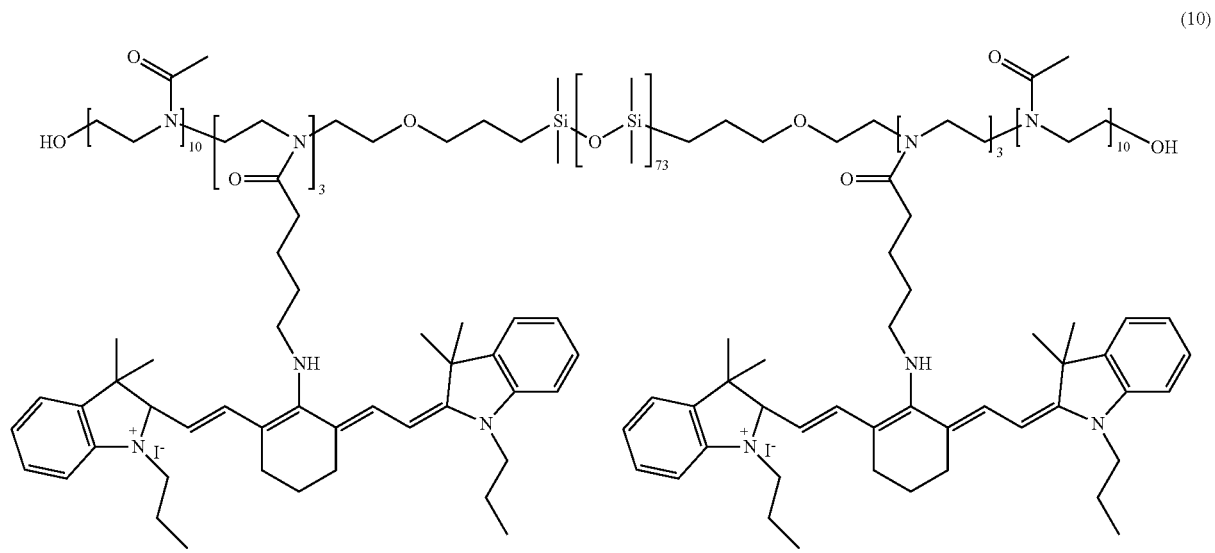

To a solution of polymer (4) (82.0 mg, 0.01 mmol) in acetonitrile (2 mL) was added DIPEA (0.04 mL, 0.3 mmol), followed by addition of compound (10A) (60 mg, 0.09 mmol)

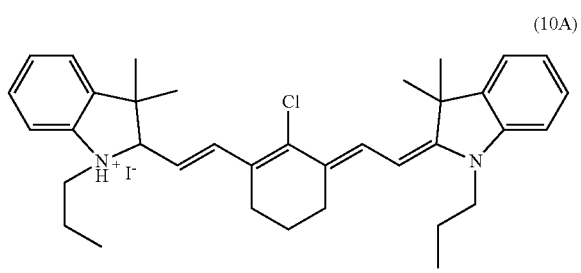 [SMILES: CCCN1/C(=C/C=C2\CCCC(/C=C/C3N(CCC)c4ccccc4C3(C)C)=C2Cl)C(C)(C)c2ccccc21 ; [I-]]

The reaction mixture was heated to 80° C. and stirred at same temperature for 2 h. Then solvent was removed by evaporation to obtain a residue. The residue was purified by ultra-filtration with cellulose regenerated membrane (a cut off at 10000 dalton) using ethanol/water (80:20, v/v, at least for four times) as eluent to produce 72 mg of compound (10) as a dark green solid. Yield: 60%. Maximal fluorescence emission wavelength of compound (10) was determined (excitation wavelength of 635 nm) to be 705 nm.

Example 11

Preparation of

To a solution of poly(dimethylsiloxane), bis(hydroxyalkyl) terminated (5.6 g, 1 mmol) in toluene (25 mL) was added 2,6-lutidine (0.35 mL, 3 mmol), followed by addition of a solution of trifluoromethanesulfonic anhydride (0.4 mL, 2.4 mmol) in hexane (2.5 mL) dropwise in ice bath under argon. The reaction mixture was stirred at same temperature for 3 h. Then solvent was removed under vacuum to give an active intermediate as a yellow oil. The oil was dissolved in a mixed solvent of chloroform (15 mL) and acetonitrile (20 mL). Monomer 2-methyl-oxazoline (3.4 mL, 40 mmol) was added at rt. The reaction mixture was heated to 60° C. again and stirred at some temperature for 48 h. Then it was quenched with sodium azide (2.6 g, 40 mmol) at r.t. Solvent was removed by evaporation to afford a residue. The residue was purified by ultra-filtration with cellulose regenerated membrane (a cut off at 5000 dalton) using ethanol/water (80:20, v/v, at least for four times. In the first time, a 5 ml of saturated NaHCO₃ solution was added) as eluent to produce 6.5 g compound (11) as a slightly yellow solid. Yield: 72%, 1HNMR (400 MHz, CDCl3) δ 3.25-3.70(m, 160H), 2.05-2.21(m, 120H),1.56(m, 4H), 0.50(m, 4H), −0.02-0.20(m, 444H)ppm.

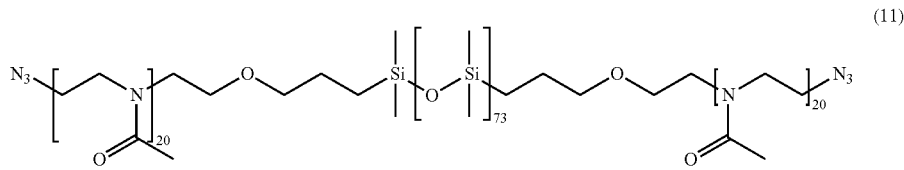

Example 12

Preparation of

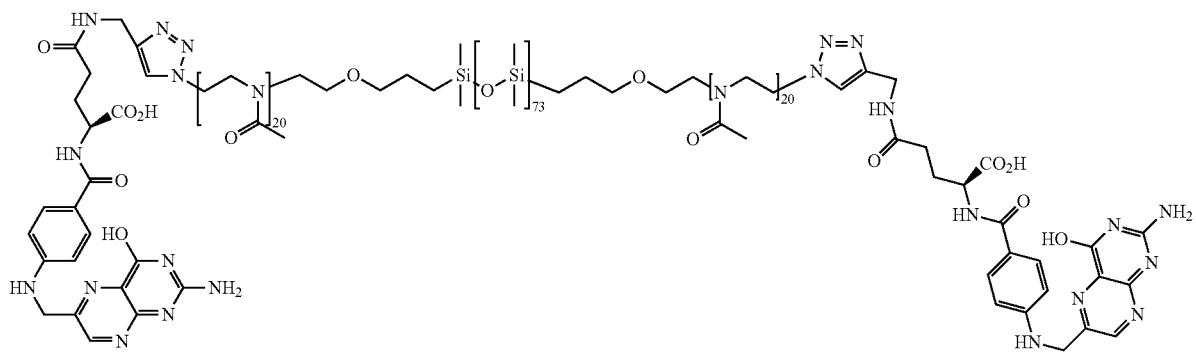

(12)

To a solution of polymer (11) (440 mg, 0.05 mmol) in DMF (5 mL) was added N,N,N',N'',N''-pentamethyldiethylenetriamine (PMDETA, 17.3 mg, 0.1 mmol), followed by addition of the folate derivative (12a) (59 mg, 0.12 mmol)

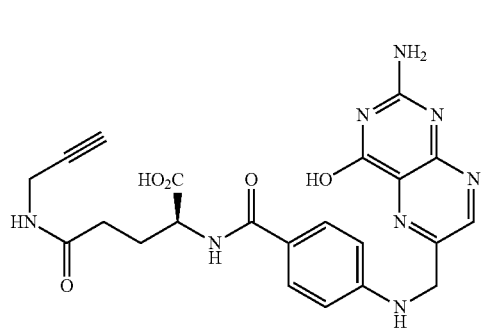

(12a)

and CuBr (14.3 mg, 0.1 mmol) successively at r.t. under argon. The reaction mixture was stirred at r.t. for 24 h. Then it was exposed to air and the solution was passed through a column of neutral alumina. DMF was removed under vacuum to afford a residue. The residue was purified by ultra-filtration with cellulose regenerated membrane (a cut off at 5000 dalton) using ethanol/water (80:20, v/v, at least for four times) as eluent to produce 245 mg compound (12) as a slightly yellow solid. Yield: 50%. 1HNMR (400 MHz, CD3OD) δ 8.72(m, 2H), 7.90(m, 2H), 7.71(m, 4H), 6.74(m, 4H), 4.20-4.90(m, 14H), 3.35-3.70(m, 160H), 1.90-2.25(m, 128H), 1.61(m, 4H), 0.58(m, 4H), 0.05-0.14(m, 444H)ppm.

Preparation of the Self-assembled Particles

General Methods of Preparation

The amphiphilic polymers of the invention i.e. Formulas (I)-(II) are used as components for the preparation of self-assembled particles, in particular micelles and vesicles. In some embodiments, the self-assembled particles comprise an independent therapeutic or diagnostic agent, or oligonucleotide. The self-assembled particles are obtainable by the following methods:

A. Nano-Precipitation

One or more amphiphilic polymer components is dissolved in an organic solvent (for example, ethanol) under stirring. An aqueous solution (e.g. PBS) is then added dropwise to this solution. After 2 h-24 h of continuous stirring, the solution is filtered through filters of a defined pore size (e.g. Millex-GV, 0.22 μm; Millipore) to produce a homogenous population of a self-assembled particle. This method is particularly preferred for the preparation of micelles. The organic solvent is removed by evaporation. Further purification is conducted over a size exclusion column (e.g. Sepharose 2B).

The final concentration of the amphiphilic polymer components in the self-assembled particle solution ranges from CMC (critical micelle concentration) to about 50 mg/mL.

Organic solvents used in the method above may be selected from, but are not limited to, water-miscible organic solvents such as polar protic solvents, for example alcohols such as methanol, ethanol, isopropanol, n-propanol, n-butanol or polar aprotic solvents such as THF, DMF, 1,4-dioxane, DMSO, acetone, acetonitrile, Dimethoxyethane DME. Aqueous solutions used in the method above may be selected from, but are not limited to bi-distilled water; sodium chloride solution (such as 9% in wt.); biological buffers such as PBS buffer, Tris buffer; and other inorganic salt solutions such as ammonium chloride solutions.

B. Film Rehydration

One or more amphiphilic polymers are dissolved in organic solvent. The solvent is evaporated under high vacuum and the resulting polymer film is rehydrated in aqueous solution, then extruded through a polycarbonate filter (e.g. 0.2 mm pore size) and then purified over a size exclusion column (e.g. Sepharose 2B). This method is particularly preferred for the preparation of vesicles.

The final concentration of the amphiphilic polymer components in the self-assembled particle solution ranges from CMC (critical micelle concentration) to about 50 mg/mL.

Organic solvents used in this method may be selected from, but are not limited to, volatile organic solvents such as dichloromethane, acetone, chloroform, THF, ethanol, methanol. The aqueous solutions used in this method may be selected from, but are not limited to bi-distilled water; sodium chloride solution (e.g. 9% in wt.); biological buffers such as PBS buffer, Tris buffer; and other inorganic salt solutions such as ammonium chloride solutions.

In both methods A and B, independent therapeutic diagnostic agents or oligonucleotides may be incorporated into the self-assembled particles as follows: agents which are soluble in organic solvent (for example, a hydrophobic drug such as taxol) are dissolved in same solvent used for dissolving the amphiphilic polymer. Water-soluble agents such as oligonucleotides are pre-dissolved in aqueous solution.

C. Solid Rehydration (Bulk Swelling Method)

One or more of the amphiphilic polymers in the form of a bulk powder is directly added to an aqueous solution. The mixture is continuously stirred until complete hydration of the polymer is observed. The resulting mixture is then extruded through a polycarbonate filter (e.g. 0.2 mm pore size filter) and then purified over a size exclusion column (e.g. Sepharose 2B).

The self-assembled particles of the invention are characterized by methods known in the art. Dynamic light scattering (DLS) measurements and transmission electron micrographs (TEM) analysis may be used, for example, to determine the size of the particles. The average diameter of the particles may be determined with DLS and further confirmed by TEM measurements. DLS measurements are performed on samples of self-assembled particles at 25° C. on a Malevern Zetasizer NanoS (ZEN 1600). TEMs are acquired using a FEI CM 200 microscope operating at an accelerating voltage of 200 kV. For TEM analysis, a sample of the self-assembled particles is first dissolved in distilled water (1 wt % in water) and then placed on a copper grid covered by a nitroglycerin film coated with carbon. A staining agent is then added (2% uranyl acetate).

Example 13

Micelles Comprising Amphiphilic Polymer (6)

To prepare the micelles, 5 mg of the amphiphilic polymer (6) is dissolved in 50 µl, of ethanol under stirring. To this solution is added, dropwise, 0.95 mL of phosphate-buffered saline (PBS). After 2 h of continuous stirring, the solution is filtrated through filters of a defined pore size (Millex-GV, 0.22 µm; Millipore) to provide a homogenous population of micelles.

Example 14

Micelles Comprising Amphiphilic Polymer (6) and (13)

To prepare the micelles, 5 mg of the amphiphilic polymer (13) and 5 mg of amphiphilic polymer (6) are dissolved in 50 µl, of ethanol under stirring. To this solution is added dropwise, 0.95 mL of phosphate-buffered saline (PBS). After 4 h of continuous stirring, the solution is filtered through filters of a defined pore size (Millex-GV, 0.22 µm; Millipore) to provide a homogenous population of micelles.

Example 15

Vesicles Comprising Amphiphilic Polymer (6) and (13)

To prepare the vesicles, 10 mg of polymer (6) and 10 mg of polymer (13) are dissolved in 10 mL of chloroform. The solvent is evaporated under high vacuum to provide a dry polymer film and the resulting polymer film is rehydrated in 20 mL of 1×PBS buffer (PH=7.4) for 12 h with stirring, then extruded through a polycarbonate filter (0.2 mm pore size) to produce vesicles.

Example 16

Micelles Comprising Amphiphilic Polymers (13) and (12)

To prepare the micelles, 5 mg of the amphiphilic polymer (13) and 0.5 mg of the amphiphilic polymer (12) are dissolved in 50 µl, of ethanol under stirring. To this solution is added, dropwise, 0.95 mL of phosphate-buffered saline (PBS). After 6 h of continuous stirring, the solution is filtered through filters of defined pore size (Millex-GV, 0.22 µm; Millipore) to provide a homogenous population of micelles.

Example 17

Micelles Comprising Amphiphilic Polymers (13) and (12) Encapsulating Paclitaxel

To prepare the micelles, 5 mg of the amphiphilic polymer (13), 0.5 mg of the amphiphilic polymer (12) and 1.5 mg of paclitaxel are dissolved in 50 µL of ethanol under stirring. 0.95 mL of phosphate-buffered saline (PBS) is added dropwise to the solution. After 6 h of continuous stirring, the solution is filtered through filters of defined pore size (Millex-GV, 0.22 µm; Millipore) to produce a homogenous population of micelles. The micelles are further purified over a size exclusion column to remove unencapsulated paclitaxel using PBS buffer as an eluent. The resulting solution is lyophilized to produce solid nanoparticles.

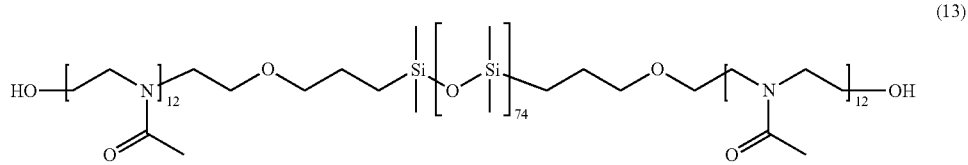

(13)

Example 18

Micelles Comprising Amphiphilic Polymers (9) and (12)

To prepare the micelles, 5 mg of polymer (9) (conjugated with doxorubicin), 0.5 mg polymer (12) are dissolved in 50 µL of ethanol under stirring. 0.95 mL of phosphate-buffered saline (PBS) was added dropwise to this solution. After 5 h of continuous stirring, the solution is filtered through filters of a defined pore size (Millex-GV, 0.22 µm; Millipore) to produce a homogenous population of micelles.

Example 19

Micelles Comprising Amphiphilic Polymer (14) and (12) Encapsulating Doxorubicin Hydrochloride (14)

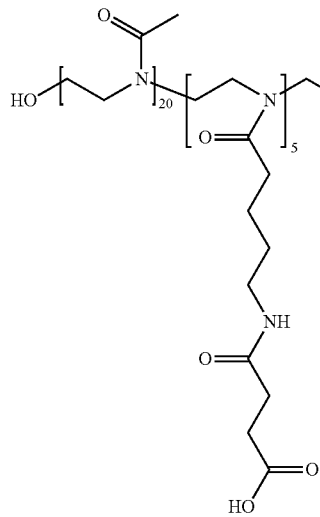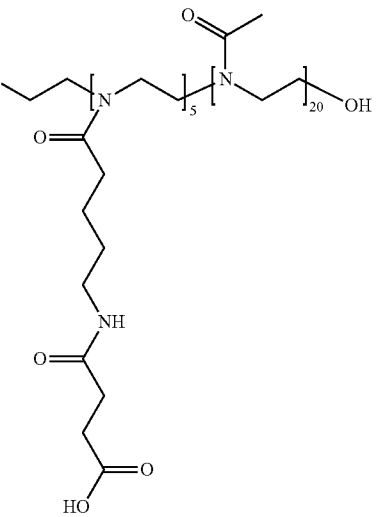

To prepare the micelles, 5 mg of the polymer (14), 0.5 mg of the polymer (12) and 1.5 mg of doxorubicin hydrochloride are dissolved in 50 μL of ethanol under stirring. 0.95 mL of phosphate-buffered saline (PBS) is added dropwise to this solution. After 6 h of continuous stirring, the solution is filtered through filters of a defined pore size (Millex-GV, 0.22 μm; Millipore) to produce a homogenous population of micelles. The micelles are further purified over a size exclusion column to remove unencapsulated doxorubicin using PBS buffer as an eluent. The resulting solution is then lyophilized to produce solid nanoparticles.

Example 20

Micelles Comprising Amphiphilic Polymers (12) and (13) Encapsulating a Rhodamine B Derivative To prepare the micelles, 5 mg of polymer (13), 0.5 mg of polymer (12) and 0.1 mg of a rhodamine B derivative are dissolved in 50 μl, of ethanol under stirring. 0.95 mL of phosphate-buffered saline (PBS) is added dropwise to this solution. After 6 h of continuous stirring, the solution is filtered through filters of defined pore size (Millex-GV, 0.22 μm; Millipore) to produce a homogenous population of micelles.

Example 21

Micelles Comprising Amphiphilic Polymers (4) and (12) and Encapsulating siRNA siRNA-loaded micelles based on the amphiphilic polymers (4) and (12) are prepared by aqueous self-assembly. The polymers are each dissolved in 200 μl ethanol under stirring to provide 2.5% (w/v) solutions. The two polymer solutions are then combined so as to obtain a desired N/P ratio (the ratio of moles of the amine groups of the polymer (4) to the moles of phosphate of the oligonucleotide), meanwhile, the amphiphilic polymer mixture also has a 0.5 mol % content of polymer (12). A desired amount of this mixture is subsequently added to 100 μl of 10 mM PBS buffer containing 40 pmol of siRNA. The resulting mixture is vortexed for 2 min followed by gentle stirring for 1 h at room temperature.

Example 22

Micelles Comprising Amphiphilic Polymers (5) and (12) and Encapsulating siRNA, Targeted Gene Delivery Model siRNA-loaded micelles based on the amphiphilic copolymers (5) and (12) were prepared in analogy to the method described in Example 21. The two polymers are dissolved in ethanol and gently mixed with 100 μl of 10 mM PBS pH 7.4 containing 40 pmol siRNA to obtain a desired N/P ratio of 5. The resulting mixture was further incubated for 1 h at room temperature.

The siRNA used for micelle-loading were Cy3-fluorescently labeled anti-GFP siRNA, anti-GFP siRNA and siRNA of random sequence (Microsynth, Balgach, Switzerland). The siRNA sequence targeting GFP is 5-GCA GCA CGA CUU CUU CAA G-3' (sense) and 5-CGU CGU GCU GAA GAA GUU C-3' (antisense).

The zeta potential of the resulting micelles ("targeted micelles") was determined by measuring electrophoretic mobility. The particle surface of micelles formed prior to addition of the (non-labelled) siRNA was also determined to be slightly positive (+4 mV) indicating that most of the positive charge is shielded by the outer PMOXA shell. The micelles comprising the siRNA, prepared at N/P of 5, were determined to have a slightly positive charge (+4 mV) and small particle size (diameter of 21±3 nm). Nanoparticles with almost neutral surface charge (zeta potential between −10 and +10 mV) are generally less likely to affect immunological reactions in vivo. To evaluate the long-term stability, these micelles were stored in PBS (pH=7.4) at 37° C. for 4 days and the size and zeta potential were measured.

There was no significant change in the average diameter of the micelles were observed during the study.

The cellular uptake efficiency of Cy-3 fluorescent-labelled siRNA loaded targeted micelles (comprising amphiphilic polymers (5) and (12)) as well as non-targeted micelles (comprising only the amphiphilic polymer (5) micelles) on cancerous folate receptor (FR) positive (HeLa) or normal FR-negative (HEK293) cells was studied. Green fluorescent protein (GFP) expressing HeLa cells were transfected in 24-well plates (Corning) using the prepared micelles and as a positive control Lipofectamin™ RNAiMax prepared according to the manufacturers protocol. Complexes were prepared inside the well after which cells (10'000 cells/well) and medium were added. The cells were washed after 24 h with PBS and fresh growth medium was added following incubation at 37° C. for additional 48 h. Quantification of downregulation of target gene expression was analyzed by western blot analysis.

The western blot analysis results demonstrated significant cellular uptake of the Cy3 fluorescent-labelled siRNA in HeLa cells treated with the folic acid receptor targeted micelles after a 24 h incubation time. A weaker signal for Cy3-labelled siRNA was observed in the HeLa cells treated with the non-targeted complexes (suppression to 92±4.2%). The normal FR-negative HEK203 cells demonstrated no significant cellular uptake of the Cy3-labelled anti-GFP siRNA even after 24 h of incubation. GFP expression was determined to be suppressed to 69±5.5% (i.e. a ca. 31% knock-down efficiency) with these targeted micelles.

A viability assessment of the HeLa cells treated with the micelles was also examined at various concentrations for 24 h and 48 h periods. It was found that cell viability is still above 90% (relative to control of untreated cells) after 48 h incubation with micelles at a concentration of 50 μm i.e. ten times higher than the used in the cellular uptake experiments.

The interaction afforded by the presence of multiple positively-charged amino groups featured in the amphiphilic polymer (5), with the negatively charged nucleotide material (i.e. the siRNA) is thought to enable the efficient encapsulation, and thereby protection of the said gene material from enzymatic degradation and other physiological processes. These micelles, having as described above a net neutral charge, good colloidal stability in serum and low cytotoxicity, are thus suitable for use as carriers for gene delivery. At the same time, these micelles, which also comprise a ligand-labelled amphiphilic polymer are able to selective deliver the siRNA and thereby improved transfection efficiency. Similar effects may be expected also for self-assembled particles prepared from amphiphilic polymers (6), (7), and (8) as described above.

Example 23

Targeting of Human Xenograft Tumors in Mice

Targeting micelles comprising 70 wt % of an amphiphilic polymer of formula (15) and 20 wt % of an amphiphilic polymer of formula (16) comprising tumor-receptor specific targeting ligands, i.e. a folate at the terminal positions and 10 wt % of an amphiphilic polymer of formula (17) comprising a rhodamine B dye at the terminal positions were prepared by nanoprecipitation method in analogy to the general methods described and previous examples, e.g. Example 20. As a control, non-targeting micelles comprising 90 wt % of (15) and 10 wt % of (17) were also prepared using such methods. The size of the resulting micelles are approximately 20-120 nm in diameter, as determined by DLS

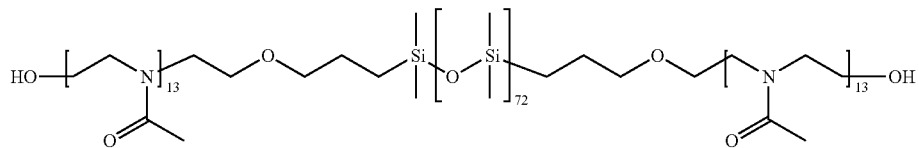

(15)

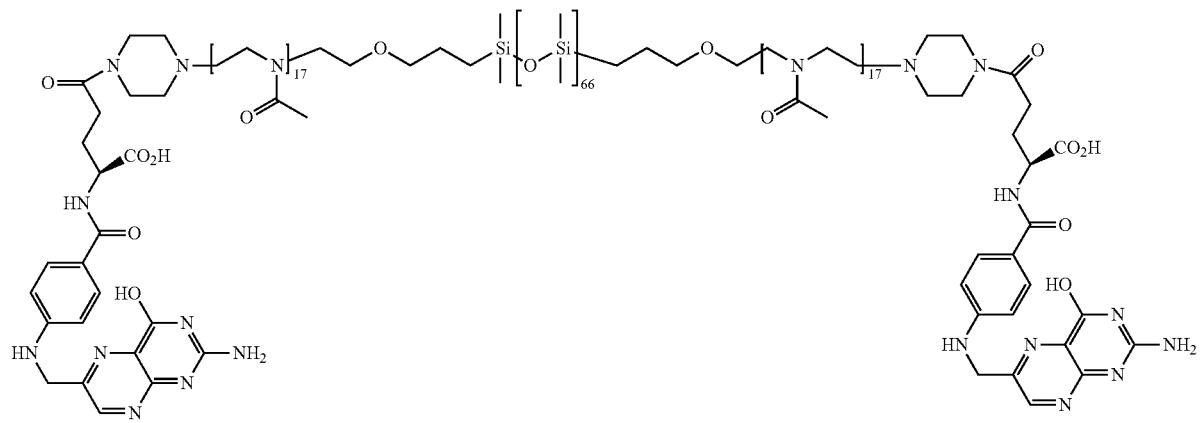

(16)

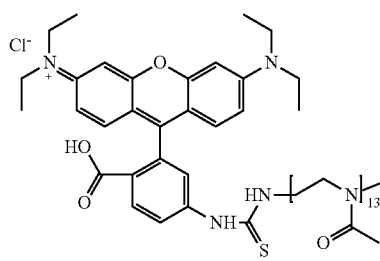
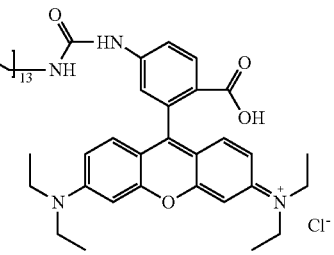

Xenograft cancer models in laboratory mice (human colon carcinoma LS174 mouse xenografts) with implanted human tumor cells were utilized in accordance to established protocols. Xenograph flank tumors were induced in 6-8 weeks old NOD.SCID mice. Tumor cells were collected and washed in PBS buffer solution. A 100 μL volume containing 2 million cells was injected subcutaneously on the right flank of mice. When tumor mass reached 0.5 cm in length in any direction, 200 μL of ligand-equipped and fluorescence-labelled micelles as prepared above (50 mg/kg body weight) were injected into tail vein. As a control, select mice were also injected with the non-folate targeting micelles. The mice were imaged by NighOWL (in vivo imaging) at 1 h, 2 h, 4 h, 8 h and 24 h intervals, and then sacrificed. The organs were also isolated and imaged.

In result, a strong uptake at the tumor boundary for targeting micelles comprising the amphiphilic polymer (16) was observed (FIG. 1, 1A); in contrast only weak uptake of the control micelles prepared without the folic acid targeting amphiphilic polymer component was observed (FIG. 1, 1B). Further analysis of the fluorescent images also revealed that that with the non-targeted micelles, accumulation occurred predominantly at the border zone of the tumor, whereas with the targeted micelles, an enhanced uptake at locations deeper inside the tumor could be achieved.

The invention claimed is:

1. A self-assembled particle comprising at least one amphiphilic polymer wherein the self-assembled particle is selected from:
   (a) a self-assembled particle comprising at least one amphiphilic polymer of the Formula (I):

B-(L$_0$-A-Z)$_n$ wherein
   n is 1 or 2;
   B is a hydrophobic polysiloxane segment;
   L$_0$ is a divalent linker segment;
   A is a hydrophilic poly-2-oxazoline copolymer segment; and
   Z is a terminal group or a linker conjugated to a ligand;
   or
   (b) a self-assembled particle, which is a micelle, comprising at least one amphiphilic polymer of the Formula (II)

B-(L$_0$-C-Z)$_n$ wherein B is a hydrophobic polysiloxane segment;
   L$_0$ is a divalent linker segment;
   C is a hydrophilic poly-2-oxazoline homopolymer segment; and
   Z is a terminal group or a linker conjugated to a ligand;
   optionally, wherein the self-assembled particle comprises at least one amphiphilic polymer of Formula (II) wherein Z is a linker conjugated to a ligand;
   or
   c) a self-assembled particle comprising at least one amphiphilic polymer of the Formula (II)

B-(L$_0$-C-Z)$_n$ wherein B is a hydrophobic polysiloxane segment;
   L$_0$ is a divalent linker segment;
   C is a hydrophilic poly-2-oxazoline homopolymer segment; and
   Z is a terminal group;
   and further comprising at least one amphiphilic polymer of Formula (II)

B-(L$_0$-C-Z)$_n$ wherein B is a hydrophobic polysiloxane segment;
   L$_0$ is a divalent linker segment;
   C is a hydrophilic poly-2-oxazoline homopolymer segment; and
   wherein Z is a linker conjugated to a ligand selected from an antibody, an antigen-binding fragment (fab), a single domain antibody, an oligonucleotide, a polypeptide and a carbohydrate; or wherein Z is a linker conjugated to a receptor-specific ligand.

2. The self-assembled particle according to claim 1, wherein the self-assembled particle comprises an amphiphilic polymer of Formula (I), and further comprises at least one amphiphilic polymer of the Formula (II):

B-(L$_0$-C-Z)$_n$ wherein B, L$_0$, Z and n are as defined in claim 1 and wherein C is a hydrophilic poly-2-oxazoline homopolymer segment.

3. The self-assembled particle according to claim 1, wherein the self-assembled particle comprises an amphiphilic polymer of Formula (I), and wherein the hydrophilic poly-2-oxazoline copolymer segment A of the amphiphilic polymer of Formula (I) is conjugated with a diagnostic agent, a therapeutic agent, or a ligand.

4. The self-assembled particle according to claim 1, wherein the self-assembled particle comprises an amphiphilic polymer of Formula (I), and wherein the hydrophilic poly-2-oxazoline copolymer segment A of the amphiphilic polymer of Formula (I) is obtainable from the copolymerization of at least two 2-substituted 2-oxazoline monomers, wherein at least one of the monomers is a 2-alkyl-2-oxazoline or a 2-aryl-2-oxazoline.

5. The self-assembled particle according to claim 1, wherein the self-assembled particle comprises an amphiphilic polymer of Formula (I), and wherein the hydrophobic polysiloxane segment B of the amphiphilic polymer of Formula (I) is a polydimethylsiloxane segment; and wherein the poly-2-oxazoline copolymer segment A comprises at least one poly-2 methyl-oxazoline block within the copolymer segment, and wherein Z is a terminal group.

6. The self-assembled particle according to claim 2 wherein the hydrophobic polysiloxane segment B of the amphiphilic polymer of Formula (II) is a polydimethylsiloxane, and wherein the segment C is a poly-2-methyl-oxazoline.

7. The self-assembled particle according to part (a) or part (c) of claim 1, wherein the particle is a micelle or a vesicle.

8. The self-assembled particle according to claim 1, comprising a therapeutic agent, a diagnostic agent or an oligonucleotide or combinations thereof, which is not covalently bonded to the self-assembled particle.

9. An amphiphilic polymer of the general Formula (I)

B-(L$_0$-A-Z)$_n$ wherein, n is 1 or 2;

B is a hydrophobic polysiloxane segment;

L$_0$ is a divalent linker segment;

A is a hydrophilic poly-2-oxazoline copolymer segment; and

Z is a terminal group or a linker conjugated to a ligand; and wherein (a) L$_0$ is of formula R$_8$(Q)$_u$, wherein R$_8$ is selected from an alkylene or arylene group containing 1 to 20 carbon atoms and an alkylene or arylene group containing 1 to 20 carbon atoms interrupted by one or more of the heteroatoms O, N, S;

Q is selected from —O—, —S—, —S—S—, —NR$_9$—, —NHC(O)—, —C(O)NH—, —OC(O)NH—, —NHC(O)O—, —OC(O), C(O)O—, —NHC(O)NH—, —SC(O)—, —C(O)S—, —NHC(S)NH—,

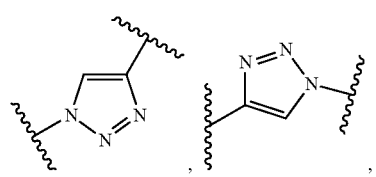

wherein R$_9$ is hydrogen or C1-C4 alkyl, and u is 0, 1, or 2;

(b) Z is a terminal group of formula —X$_1$-Q$_0$ or a linker conjugated to a ligand of formula -L$_3$-R$_{11}$, wherein X$_1$ is selected from —O—, —S—, —NH—, —NR$_{10}$—,

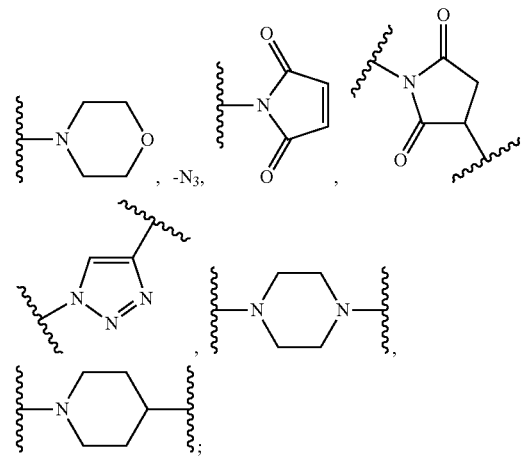

Q$_0$ is absent or selected from H, unsubstituted or substituted alkyl, alkenyl, aralkyl, alkynyl, heterocyclyl, aryl, —C(O)—(CH$_2$)$_q$—COOH, —C(O)O—R$_{10}$, —(CH$_2$)$_q$—C(O)O—R$_{10}$, —C(O)R$_{10}$, —NHC(O)—(CH$_2$)$_q$—N$_3$, —(CH$_2$)$_q$—N$_3$, or —SR$_{10}$, wherein R$_{10}$ is an unsubstituted or substituted alkyl, alkenyl, or aralkyl group, and q is an integer from 1 to 10;

L$_3$ is —S—, —O—, —OC(O)—, —OC(O)NH—, —NHC(O)—, —NHC(O)NH, —NHC(S)NH—, —NHC(O)O—,

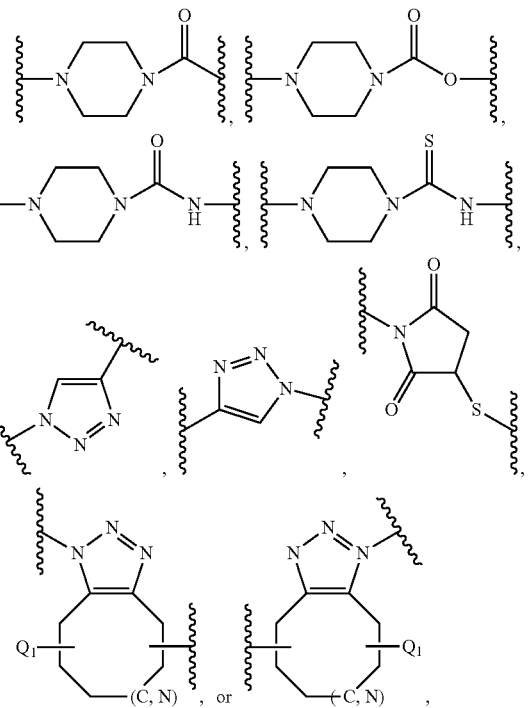

or wherein Q$_1$ represents one or more substituents;

R$_{11}$ is a ligand selected from a small molecule, an antibody, an antigen-binding fragment (fab), a single domain antibody, an oligonucleotide, and a carbohydrate;

(c) A is a hydrophilic poly-2-oxazoline copolymer segment of Formula (I-a):

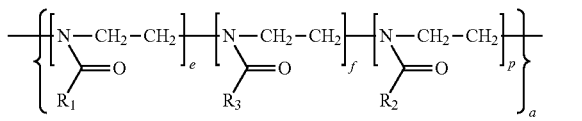

wherein
$R_1$ and $R_3$ are independently selected from a linker conjugated to a therapeutic agent, a diagnostic agent, a ligand, and a linker comprising a functional group selected from an amine, an azide, an alkyne, an aldehyde, an acetal, an alcohol, a carboxylic acid, an activated carboxylic acid, an oxyamine, a ketone, a ketal, an ester, a maleimide, a vinyl sulfone, an orthopyridyl disulfide and a chloroformate;
$R_2$ is a C1-C20 alkyl or aralkyl group;
e and f are integers independently selected from 0-500, provided that e and f are not simultaneously selected as 0;
p is an integer selected from 2-500;
a is selected from (1) a random copolymer wherein the units as defined by the integers e, f and p are in random, and (2) a block copolymer wherein the units as defined by the integers e, f, and p are sequential segments.

10. The amphiphilic polymer according to claim 9, wherein A is a hydrophilic poly-2-oxazoline copolymer segment of Formula (I-b):

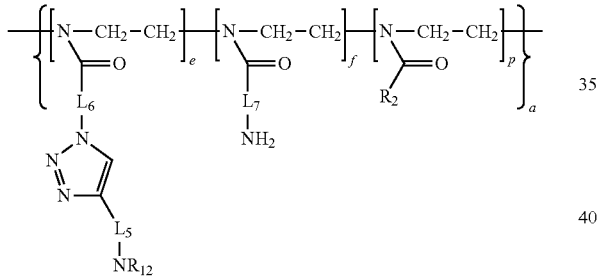

wherein $L_5$, $L_6$ and $L_7$ are independently selected from C1-C20 alkylene, C4-C12 arylene, and C1-C20 alkylene or C4-C12 arylene interrupted by one or more of the heteroatoms O, N, S;
$R_{12}$ is selected from —H(H), —(H)$R_{13}$, —($R_{13}$)$_2$ and —($R_{13}$)$_2$$R_{14}$X, wherein $R_{13}$ and $R_{14}$ are independently selected from substituted or unsubstituted C1-C20 alkyl and substituted or unsubstituted aralkyl, and wherein X is a negative counterion;
and wherein
Z is a terminal group selected from —OH, —NH$_2$,

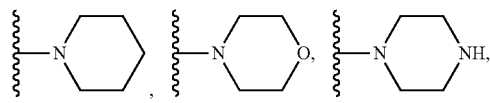

—OR$_{15}$, —NR$_{15}$R$_{16}$, and —SR$_{15}$, wherein R$_{15}$ and R$_{16}$ are independently selected from unsubstituted or substituted alkyl, alkenyl, and aralkyl.

11. The amphiphilic polymer according to claim 10, wherein f is 0 and wherein A is a hydrophilic poly-2-oxazoline copolymer segment of Formula (I-c):

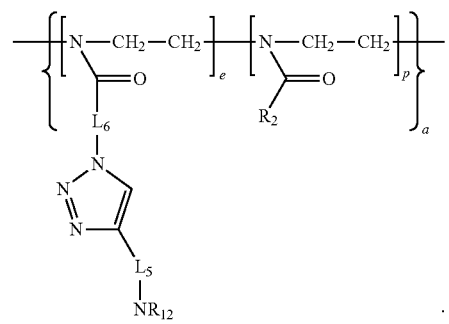

12. The amphiphilic polymer according to claim 9, wherein A is a hydrophilic poly-2-oxazoline copolymer segment of Formula (I-d):

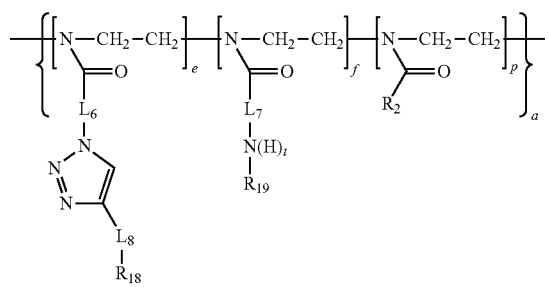

wherein
$R_{18}$ and $R_{19}$ are independently selected for each monomeric unit from a diagnostic agent, a therapeutic agent, a ligand, and a substituent selected from hydrogen, C1-C20 alkylene, C1-C20 arylene, provided that for at least one monomeric unit, $R_{18}$ and/or $R_{19}$ is a diagnostic agent, therapeutic agent or a ligand;
$L_6$ and $L_7$ are independently selected from C1-C20 alkylene, C4-C12 arylene, and C1-C20 alkylene or C4-C12 arylene interrupted by one or more of the heteroatoms O, N, S;
$L_8$ is a divalent linker of formula —R$_{20}$(Y)$_s$, wherein $R_{20}$ is a C1-C20 alkylene or arylene, or a C1-C20 alkylene or arylene interrupted by one or more of heteroatoms O, N, S; Y is —S—S—, —NHC(O)—, —C(O)NH—, —OC(O)NH—, —NHC(O)O—, —OC(O)—, —OC(O)O—, —C(O)O—, —NHC(O)NH—, —SC(O)—, —C(O)S—, —NHC(S)NH—, —NH— and —C(O)—NH—N=, and s is 0, 1 or 2;
t is selected from an integer of 0 or 1; and wherein
Z is a terminal group selected from —OH, —NH$_2$,

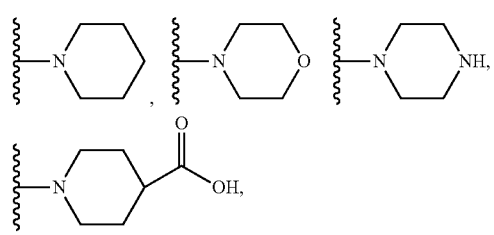

-continued

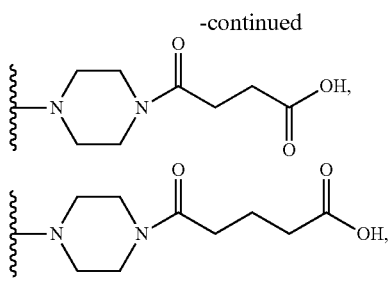

—OR$_{16}$, —NR$_{16}$R$_{17}$, —SR$_{16}$, wherein R$_{16}$ and R$_{17}$ are independently selected from unsubstituted or substituted alkyl, alkenyl, and aralkyl.

13. The amphiphilic polymer according to claim 12 wherein f is 0, and wherein A is a hydrophilic poly-2-oxazoline copolymer segment of Formula (I-e):

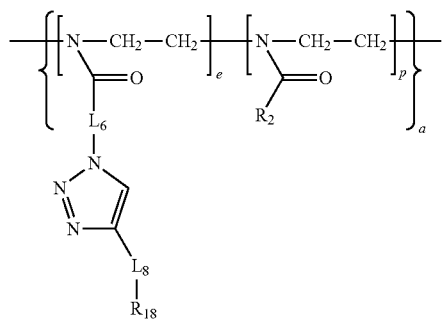

wherein
R$_{18}$ is selected independently for each monomeric unit from a therapeutic agent, selected from a chemotherapeutic or antineoplastic agent; a diagnostic agent; a substituent selected from hydrogen, C1-C20 alkylene, and C1-C20 arylene;
provided that for at least one monomeric unit, R$_{18}$ is a therapeutic agent or diagnostic agent.

14. The amphiphilic polymer according to claim 12 wherein e is 0 and wherein A is a hydrophilic poly-2-oxazoline copolymer segment of Formula (I-f):

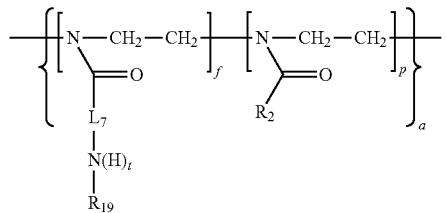

wherein
R$_{19}$ is independently selected for each monomeric unit from a therapeutic agent, selected from a chemotherapeutic or antineoplastic agent; a diagnostic agent; or a substituent selected from hydrogen, C1-C20 alkylene, and C1-C20 arylene;
provided that for at least one monomeric unit, R$_{19}$ is a therapeutic agent or diagnostic agent.

15. A method of preparing the amphiphilic polymer of claim 9, comprising a step of cationic ring-opening polymerization of a polysiloxane initiator with at least one 2-(azidoalkyl)-2-oxazoline monomer and at least one 2-alkyl-2-oxazoline or 2-aralkyl-2-oxazoline monomer.

16. The method according to claim 15, further comprising a step of azide reduction and/or a step of 1,3 dipolar cycloaddition with an alkynyl component.

17. The amphiphilic polymer according to claim 9, wherein A is a hydrophilic poly-2-oxazoline copolymer segment of Formula (I-g):

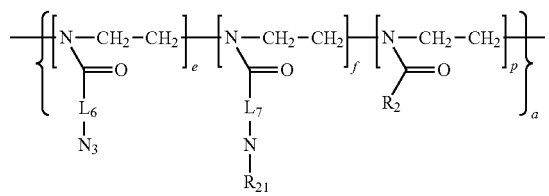

wherein
L$_6$ and L$_7$ are independently selected from C1-C20 alkylene, C4-C12 arylene, and C1-C20 alkylene or C4-C12 arylene interrupted by one or more of the heteroatoms O, N, S; and
R$_{21}$ is selected from H(H), H(R$_{22}$), (R$_{22}$)$_2$ or (R$_{22}$)$_2$R$_{23}$X, wherein R$_{22}$ and R$_{23}$ are independently selected from substituted or unsubstituted C1-C20 alkyl and substituted or unsubstituted aralkyl, and X is a negative counterion.

18. The amphiphilic polymer according to claim 17 wherein
f is 0;
A is a hydrophilic poly-2-oxazoline copolymer segment of Formula (I-h):

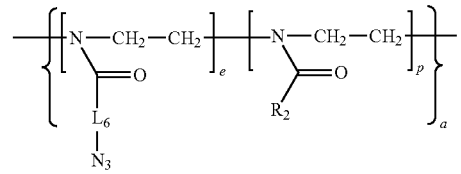

and wherein
Z is a terminal group selected from —OH, —N$_3$, —NH$_2$,

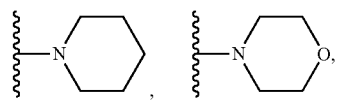

—OR$_{16}$, —NR$_{16}$R$_{17}$, —SR$_{16}$,

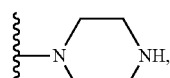

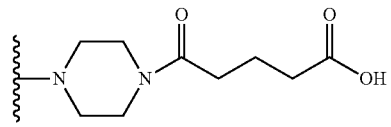

-continued

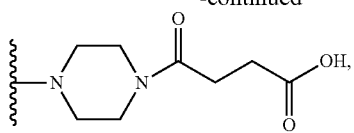

wherein $R_{16}$ and $R_{17}$ are independently selected from unsubstituted or substituted alkyl, alkenyl, and aralkyl.

19. The amphiphilic polymer according to claim 17, wherein
e is 0,
$R_{21}$ is H(H), and
A is a hydrophilic poly-2-oxazoline copolymer segment of Formula (I-i)

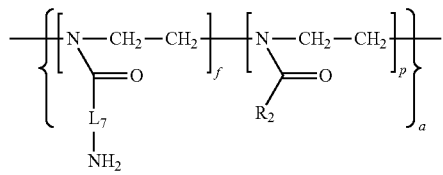

Z is a terminal group selected from —OH, —N₃, —NH₂,

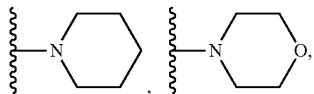

—OR$_{16}$, —NR$_{16}$R$_{17}$, —SR$_{16}$,

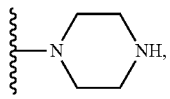

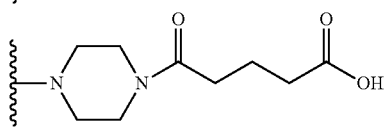

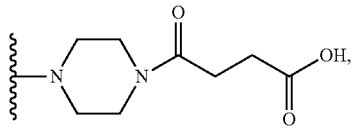

wherein $R_{16}$ and $R_{17}$ are independently selected from unsubstituted or substituted alkyl, alkenyl, and aralkyl.

20. The self-assembled particle according to claim 1, wherein:
Z is a terminal group of formula —X$_1$-Q$_0$ or a linker conjugated to a ligand of formula -L$_3$-R$_{11}$, wherein
X$_1$ is selected from —O—, —S—, —NH—, —NR$_{10}$—,

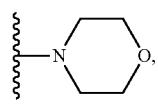

—N₃,

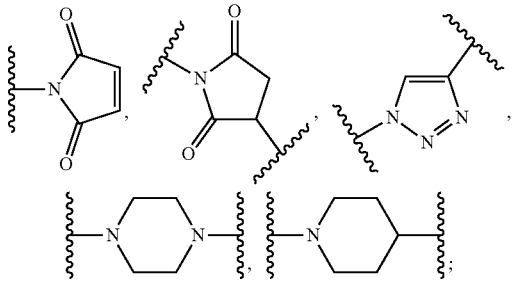

Q$_0$ is absent or selected from H, unsubstituted or substituted alkyl, alkenyl, aralkyl, alkynyl, heterocyclyl, aryl, —C(O)—(CH$_2$)$_q$—COOH, —C(O)O—R$_{10}$, —(CH$_2$)$_q$—C(O)O—R$_{10}$, —C(O)R$_{10}$, —NHC(O)—(CH$_2$)$_q$—N$_3$, —(CH$_2$)$_q$—N$_3$, or —SR$_{10}$, wherein R$_{10}$ is an unsubstituted or substituted alkyl, alkenyl, or aralkyl group, and q is an integer from 1 to 10;

L$_3$ is —S—, —O—, —OC(O)—, —OC(O)NH—, —NHC(O)—, —NHC(O)NH, —NHC(S)NH—, —NHC(O)O—,

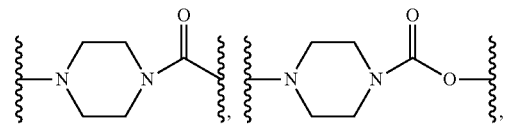

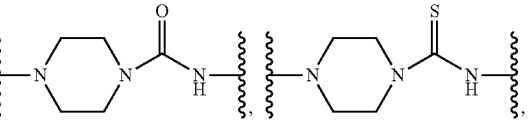

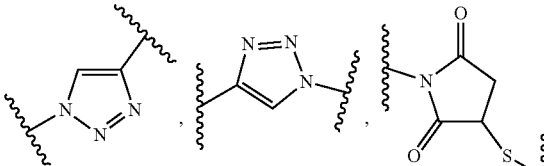

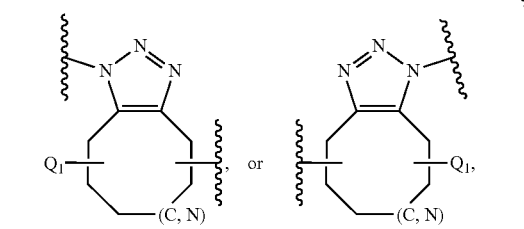

wherein Q$_1$ represents one or more substituents; and
R$_{11}$ is a ligand selected from a small molecule, an antibody, an antigen-binding fragment (fab), a single domain antibody, an oligonucleotide, a carbohydrate, and in particular from folate, biotin, or peptides;
or wherein Z is a linker conjugated to a ligand selected from a small molecule, an antibody, an antigen-binding fragment (fab), a single domain antibody, an oligonucleotide, a polypeptide and a carbohydrate.

21. The self-assembled particle according to claim 3, wherein the diagnostic agent, therapeutic agent or ligand is selected from an antibody, an antigen-binding fragment (fab), a single domain antibody, an oligonucleotide, a polypeptide or a carbohydrate.

22. The self-assembled particle according to part (a) or part (c) of claim 1, wherein the particle is a micelle.

23. The amphiphilic polymer according to claim 9, wherein $R_{11}$ is selected from folate, biotin or a peptide.

24. The amphiphilic polymer according to claim 13, wherein one or more $R_{18}$ is selected independently from doxorubicin, taxol, a fluorescent dye, a radiolabel, a PET imaging agent, an MRI imaging agent, a sensitizer, and a photoacoustic imaging agent.

25. The amphiphilic polymer according to claim 14, wherein one or more $R_{19}$ is selected independently from doxorubicin, taxol, a fluorescent dye, a radiolabel, a PET imaging agent, an MRI imaging agent, a sensitizer, and a photoacoustic imaging agent.

26. The self-assembled particle according to part (a) of claim 1, wherein the hydrophilic copolymer segment A comprises at least two 2-substituted 2-oxazoline monomers, optionally wherein the at least two 2-substituted oxazoline monomers are distributed within copolymer segment A in a random, diblock or triblock arrangement.

27. The self-assembled particle according to claim 26, wherein at least one of the two 2-substituted 2-oxazoline monomers is selected from 2-methyl-2-oxazoline, 2-ethyl-2-oxazoline, 2-propyl-2-oxazoline, 2-phenyl-2-oxazoline, and 2-(4-azidobutyl)-2-oxazoline.

\* \* \* \* \*